(12) United States Patent
Rosenberg et al.

(10) Patent No.: US 8,538,524 B2
(45) Date of Patent: Sep. 17, 2013

(54) SYSTEMS AND METHODS FOR DETECTING FAR-FIELD OVERSENSING BASED ON SIGNALS SENSED BY THE PROXIMAL ELECTRODE OF A MULTIPOLAR LV LEAD

(75) Inventors: Stuart Rosenberg, Castaic, CA (US); Tomas Svensson, Stockholm (SE); Kjell Norén, Solna (SE); Edward Karst, South Pasadena, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 267 days.

(21) Appl. No.: 13/230,482

(22) Filed: Sep. 12, 2011

(65) Prior Publication Data

US 2013/0066222 A1 Mar. 14, 2013

(51) Int. Cl.
*A61N 1/368* (2006.01)
(52) U.S. Cl.
USPC ............... 607/14; 600/518; 600/521; 607/27
(58) Field of Classification Search
None
See application file for complete search history.

(56) References Cited

U.S. PATENT DOCUMENTS

| | | |
|---|---|---|
| 6,516,225 B1 | 2/2003 | Florio |
| 6,671,548 B1 | 12/2003 | Mouchawar et al. |
| 6,711,438 B1 | 3/2004 | McClure et al. |
| 6,760,622 B2 | 7/2004 | Helland et al. |
| 7,076,300 B1 | 7/2006 | Kroll et al. |
| 7,146,213 B1 | 12/2006 | Levine |
| 7,158,829 B1 | 1/2007 | Levine |
| 7,184,816 B2 * | 2/2007 | Bjorling et al. ............... 600/509 |
| 7,184,834 B1 | 2/2007 | Levine |
| 7,212,849 B2 * | 5/2007 | Zhang et al. .................. 600/515 |
| 7,274,961 B1 | 9/2007 | Kroll et al. |
| 7,398,123 B1 | 7/2008 | Levine |
| 7,447,540 B1 | 11/2008 | Nabutovsky et al. |
| 7,653,436 B2 | 1/2010 | Schecter |
| 7,783,352 B1 | 8/2010 | Ryu et al. |
| 7,813,791 B1 | 10/2010 | Gill et al. |
| 7,826,899 B1 | 11/2010 | Ryu et al. |
| 2008/0306567 A1 | 12/2008 | Park et al. |
| 2009/0287268 A1 | 11/2009 | Nabutovsky et al. |
| 2010/0106209 A1 | 4/2010 | Gunderson et al. |
| 2010/0268059 A1 | 10/2010 | Ryu et al. |
| 2013/0060117 A1* | 3/2013 | Gunderson et al. ........... 600/374 |

FOREIGN PATENT DOCUMENTS

| | | |
|---|---|---|
| EP | 1273319 A2 | 1/2003 |
| EP | 1273319 A3 | 1/2004 |
| WO | 2010053661 A1 | 5/2010 |

* cited by examiner

*Primary Examiner* — Kennedy Schaetzle

(57) ABSTRACT

A device senses cardioelectrical signals using a right atrial (RA) lead, which might include far-field R-waves as well as near-field P-waves. The device concurrently senses events using a proximal electrode of an LV lead, which can sense both P-waves and R-waves as substantially near-field events. Suitable templates are then applied to the signals sensed via the proximal LV electrode to identify the origin of the signals (e.g. atrial vs. ventricular) so as to properly classify the corresponding events sensed in the RA as near-field or far-field events. In this manner, far-field oversensing is conveniently detected.

40 Claims, 13 Drawing Sheets

SYSTEMS AND METHODS FOR DETECTING FAR-FIELD OVERSENSING BASED ON SIGNALS SENSED BY THE PROXIMAL ELECTRODE OF A MULTIPOLAR LV LEAD

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for detecting and responding to far-field oversensing (FFOS) for use with devices equipped with multi-pole left ventricular (LV) leads.

BACKGROUND OF THE INVENTION

An implantable cardiac stimulation device is a type of implantable medical device (IMD) that delivers therapy to the heart of a patient in which the device is implanted. For example, a pacemaker recognizes various cardiac arrhythmias and delivers electrical pacing pulses to the heart in an effort to remedy the arrhythmias. An ICD additionally or alternatively recognizes ventricular tachycardia (VT) and ventricular fibrillation (VF) and delivers electrical shocks or other therapies to terminate these tachyarrhythmias. At least some pacemakers and ICDs are also equipped to deliver CRT. Briefly, CRT seeks to normalize the dyssynchronous cardiac electrical activation and resultant dyssynchronous contractions associated with congestive heart failure (CHF) by delivering synchronized pacing stimulus to both sides of the heart using left ventricular (LV) and right ventricular (RV) leads. The stimulus is synchronized to improve overall cardiac function. This may have the additional beneficial effect of reducing the susceptibility to life-threatening tachyarrhythmias.

For the purposes of detecting and responding to various arrhythmias, the implantable device tracks the heart rate of the patient by examining electrical signals associated with the contraction and expansion of the chambers of the heart. The contraction of atrial muscle tissue is triggered by the electrical depolarization of the atria, which is manifest as a P-wave in a surface electrocardiogram (ECG) and as a rapid deflection (intrinsic deflection) in an intracardiac electrogram (IEGM). The contraction of ventricular muscle tissue is triggered by the depolarization of the ventricles, which is manifest on the surface ECG by an R-wave (also referred to as the "QRS complex") and as a large rapid deflection (intrinsic deflection) within the IEGM. Repolarization of the ventricles is manifest as a T-wave in the surface ECG and a corresponding deflection in the IEGM. A similar depolarization of the atrial tissue usually does not result in a detectable signal within either the surface ECG or the IEGM because it coincides with, and is obscured by, the R-wave. Note that the terms P-wave, R-wave and T-wave initially referred only to features of a surface ECG. Herein, however, for the sake of brevity and generality, the terms are used to refer to the corresponding signals or deflections sensed internally. Also, where an electrical signal is generated in one chamber but sensed in another, it is referred to herein as a "far-field" signal. The misidentification of far-field signals as near-field events is referred to as far-field oversensing (FFOS).

The sequence of electrical events that represent P-waves followed by R-waves (or QRS complexes) followed by T-waves can be detected within IEGM signals sensed using pacing leads implanted on or within the heart. To help prevent FFOS and to more accurately detect the heart rate, the stimulation device employs one or more refractory periods and blanking periods. Within a refractory period, the device does not process electrical signals during a predetermined interval of time—either for all device functions (an absolute refractory period) or for selected device functions (a relative refractory period). As an example of a refractory period, upon delivery of a V-pulse to the ventricles, a post-ventricular atrial refractory period (PVARP) is applied to an atrial sensing channel. A first portion of the PVARP comprises a post-ventricular atrial blanking (PVAB) interval (which can also be referred to as an absolute refractory period). The PVAB is primarily provided to prevent the device from erroneously responding to far-field R-waves on the atrial channel. The PVARP concludes with a relative refractory period during which the pacemaker ignores all signals detected on the atrial channel as far as the triggering or inhibiting of pacing functions is concerned but not for other functions such as detecting rapid atrial rates or recording diagnostic information. As another example of a refractory period, upon delivery of the V-pulse to the ventricles, a ventricular refractory period (VREF) is applied to LV and RV sensing channels for preventing evoked responses (ERs) triggered by the V-pulse from being misidentified as R-waves and also for preventing the T-waves of intrinsic (i.e. non-paced) beats from being misidentified. Despite the use of PVARP and VREF intervals, FFOS can nevertheless still arise, with consequences ranging from benign to dangerous.

In particular, FFOS may arise due to incorrectly set refractory and blanking periods or due to incorrectly programmed sensitivity values. FFOS may be more likely in some anatomic configurations of the leads or in some cases of aberrant conduction. Among the adverse consequences of FFOS are inappropriate tracking of higher rates leading to pacemaker mediated tachycardia (PMT) and inappropriate mode switch leading to loss of atrial contribution to ventricular function. Moreover, FFOS in the ventricles can lead to inappropriate tachycardia therapy (either anti-tachycardia pacing (ATP) or shock therapy) that can be a prognosticator of decreased survival.

Improved techniques for correctly detecting and rejecting FFOS would be highly advantageous, and it is to this end that aspects of the invention are generally directed.

SUMMARY OF THE INVENTION

In an exemplary embodiment, a method is provided for use with an implantable cardiac stimulation device equipped with an LV lead having a proximal electrode positioned at a location sufficient to sense both atrial events and ventricular events as substantially near-field events, such as at a location in or near an atrioventricular (AV) groove of the heart of the patient via the coronary sinus (CS) or great cardiac vein (GCV). Right atrial (RA) and RV leads are both provided as well. The device senses cardioelectrical events along a primary sensing channel connected to either the RA lead or the RV lead. The events sensed on the primary sensing channel include near-field events to be detected as well as other events—such as far-field events—that need to be properly rejected. For an example where the primary sensing channel is connected to the RA lead, the near-field events are P-waves; the events to be rejected are far-field R-waves that can interfere with proper determination of the atrial rate. For an example where the primary sensing channel is connected to the RV lead, the near-field events are local R-waves generated within the RV; the events to be rejected include far-field R-waves arising from the LV as well as T-waves arising within either the LV or RV, any of which can interfere with proper determination of the ventricular rate.

Continuing with the exemplary embodiment, the device also senses cardioelectrical events along a secondary sensing channel connected to the proximal electrode of the LV lead, which is positioned at a location sufficient to sense both atrial events and ventricular events as substantially near-field events. Hence, the secondary sensing channel can sense P-waves arising from the atria as well as R-waves and T-waves arising from the ventricles. The timing and morphology of the events sensed via the proximal electrode of the LV lead will likely differ from that of the same events sensed within the RA or within the RV. Nevertheless, the signals sensed along the secondary sensing channel can be used to discriminate the events on the primary sensing channel. For the example where the primary channel is connected to the RA lead, the events sensed by the proximal electrode of the LV lead are used to distinguish P-waves arising within the atria from far-field R-waves arising within the ventricles. For the example wherein the primary channel is connected to the RV lead, the events sensed by the proximal electrode of the LV lead are used to distinguish normal R-waves arising within the RV from far-field R-waves arising within the LV and also from various types of T-waves. In either case, suitable templates are used to identify the source of the events observed on the secondary sensing channel (e.g. atrial origin vs. ventricular origin) so as to properly classify the corresponding events observed on the primary sensing channel to detect FFOS.

In a first illustrative example, the primary sensing channel is an RA bipolar channel and the secondary sensing channel is a P4 unipolar channel of a quad-pole lead. The device operates to discriminate events sensed on the RA channel by examining the morphology of corresponding events sensed contemporaneously along the P4 sensing channel. The device uses suitable templates to identify the origin of the events observed on the P4 sensing channel and, in so doing, the device likewise identifies the origin of the corresponding events on the RA sensing channel. In one particular example, the device tracks a PVARP interval on the RA channel and identifies events occurring in or near the PVARP. The events are likely either: (a) high-rate near-field P-waves indicative of a possible atrial tachyarrhythmia or (b) far-field ventricular events indicative of FFOS. For each of these RA channel events, the device identifies a corresponding (i.e. substantially contemporaneous) event on the P4 channel and compares the P4 event against a pair of templates representative of: (a) RA events sensed via P4 and (b) RV events sensed via P4. If the RA template matches better than the RV template, the device identifies the corresponding event sensed on the RA channel as a near-field P-wave. If the RV event template matches better than the RA template, the device instead identifies the corresponding event as a far-field non-ectopic R-wave. If neither template matches by a sufficient amount, the device identifies the corresponding event as a far-field ectopic (i.e. abnormal) ventricular event, such as a premature ventricular contraction (PVC).

Once the event has been properly identified, the device can take further action. For example, if the event originally sensed in or near the PVARP on the RA channel is found to be a P-wave, the device shortens the PVARP to identify other high rate P-waves and/or initiates atrial tachycardia diagnostics to confirm and respond to a possible ongoing atrial tachycardia. If the event is found to be a far-field non-ectopic R-wave, the device can extend the PVARP to reduce further FFOS. If the event is found to be a far-field ectopic R-wave, the device can increment a PVC counter. Note that the templates used for event discrimination are preferably specific to the patient and are determined in advance under clinician supervision during a follow-up session following device implant. The templates can thereafter be automatically updated—periodically or on demand—so as to account for changes in cardioelectric signal morphology within the patient. Preferably, the amount by which any particular template is automatically modified is limited so as to prevent the templates from being changed too much without clinician approval.

In a second illustrative example, the primary sensing channel is an RV bipolar channel rather than an RA channel. The device tracks a VREF interval on the RV channel and identifies events occurring in or near the VREF. The events are likely (a) high-rate near-field R-waves indicative of a possible ventricular tachyarrhythmia or supraventricular tachycardia (SVT); (b) far-field LV R-waves indicative of FFOS; (c) far-field LV T-waves indicative of FFOS; or (d) disperse T-waves. For each of these RV channel events, the device identifies a corresponding event on the P4 channel and begins the discrimination process by comparing the P4 event against templates representative of (a) normal RV events sensed via P4 and (b) T-waves sensed via P4. If the normal R-wave template matches, the device identifies the corresponding event as a high rate R-wave and initiates ventricular tachycardia diagnostics (including VT/SVT discrimination) to confirm and respond to the arrhythmia. If the normal T-wave event template instead matches, the device identifies the corresponding event as an oversensed T-wave and selectively extends the VREF to reduce further FFOS of T-waves.

If neither template matches, the device then compares the event on the P4 channel against a template representative of LV R-waves sensed via P4. If the LV R-wave template matches, the device identifies the event sensed on the RV channel as far-field R-wave from the LV and selectively extends the VREF to reduce further FFOS of LV R-waves. If the LV R-wave template does not match, the device measures the slew rate of the P4 event and compares the rate against a threshold indicative of R-waves (where R-waves have a higher slew rate than T-waves). If the slew rate exceeds the threshold, the device identifies the event sensed on the RV channel as an abnormal R-wave and initiates ventricular tachycardia diagnostics to confirm and respond to the high ventricular rate. The device can also selectively shorten the VREF to detect more high rate R-waves. If the slew rate does not exceed the threshold, the device identifies the event sensed on the RV channel as a disperse T-wave and initiates repolarization diagnostics and/or selectively extend the VREF to block further T-wave FFOS.

The dynamic adjustment of PVARP and VREF intervals achieved using these techniques preferably exploits hysteresis. Enabling dynamic PVARP and dynamic PVARP hysteresis is important in patients with hypertrophic or dilated hearts (i.e. patients likely to exhibit larger far-field R waves) who may also be predisposed to atrial tachyarrhythmias, so that atrial tachyarrhythmias can be appropriately diagnosed and treated.

System and method implementations of these and other techniques are presented herein. Although summarized primarily with respect to implementations having a quad-pole LV lead, aspects of the invention are also generally applicable to systems having other multi-pole LV leads and to systems having multi-pole RV leads or RA leads.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
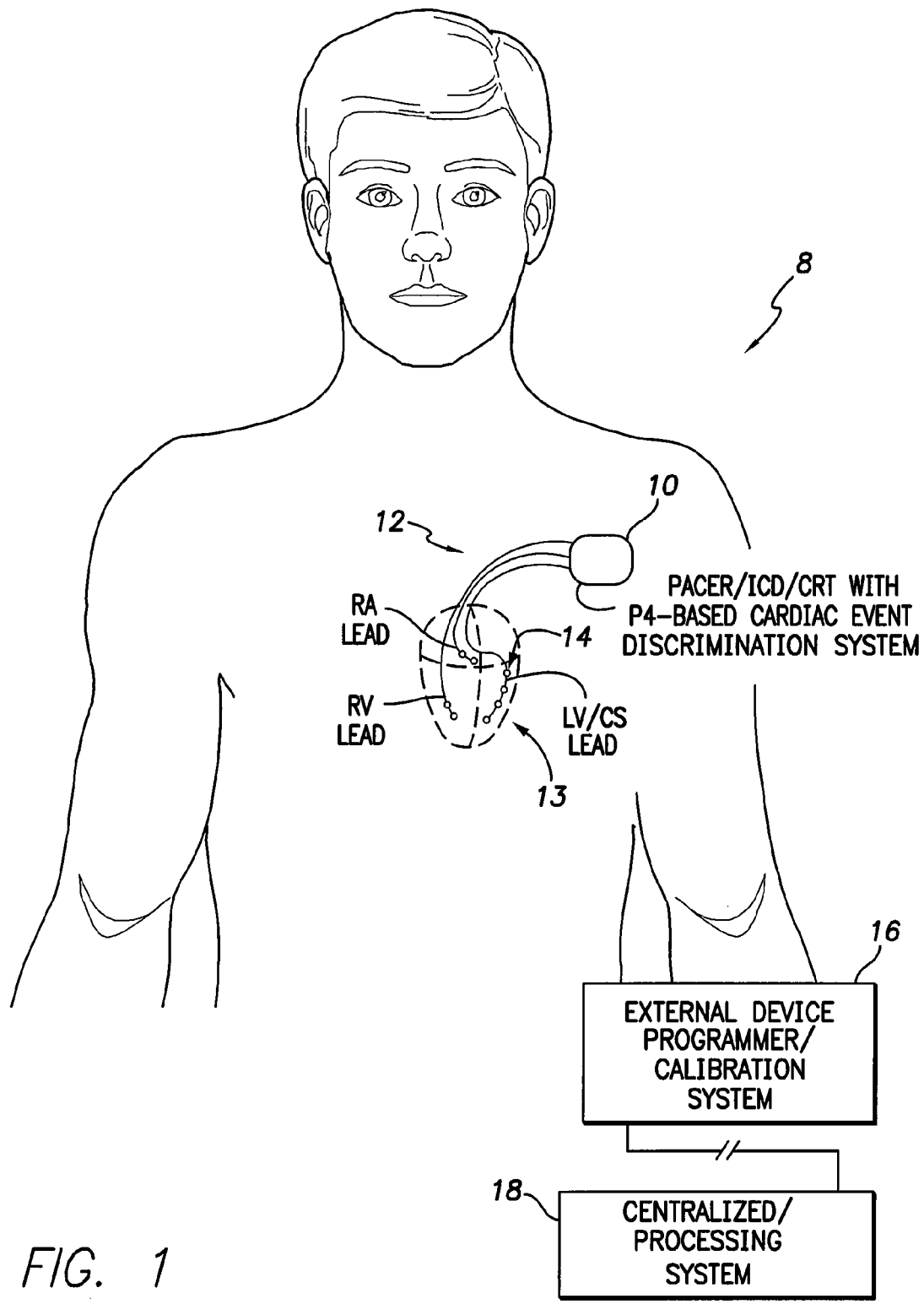
FIG. 1 illustrates components of an implantable medical system having a pacemaker, ICD or CRT device capable of discriminating cardioelectric events using signals sensed with the proximal electrode of a multipolar LV lead for use in detecting and responding to FFOS.

FIG. 1 illustrates an implantable medical system 8 capable of discriminating cardioelectrical events using signals sensed with the proximal electrode of a multipolar LV lead for use in detecting and responding to FFOS. In this particular example, the implantable medical system 8 includes a pacer/ICD/CRT 10 or other implantable cardiac rhythm management device equipped with a set of cardiac sensing/pacing leads 12 implanted on or within the heart of the patient, including a multi-pole LV lead implanted via the CS or GCV. In FIG. 1, a stylized representation of the set of leads is provided. More accurate illustrations of the leads are provided within the other figures. To illustrate the multi-pole configuration of the LV lead, a set of electrodes 13 is shown distributed along the LV lead, including a proximal electrode 14 implanted (in this particular example) in or near an AV groove of the heart.

In the examples described herein, a quad-pole (or "quadrapolar" or "quadripolar") lead is employed, such as the Quartet™ lead provided by St Jude Medical. Other suitable leads may instead be employed, including leads with more or fewer electrodes. Also, as shown, an exemplary RV lead is provided that includes an RV tip/ring electrode pair. An RA lead is also provided that includes an RA tip/ring pair. Other electrodes of various sizes and shapes may be additionally or alternatively provided, such as various coil electrodes for delivering shock therapy. Although identified as a "pacer/ICD/CRT" in FIG. 1, it should be understood that device 10 can be any suitably-equipped implantable medical device, such as a standalone pacemaker, ICD or CRT device, including CRT-D and CRT-P devices. In the following, for brevity, device 10 will be referred to simply as a pacer/CRT.

Preferably, the pacer/CRT itself performs the discrimination of the cardioelectric signals. In other implementations, however, the device might additionally or alternatively transmit pertinent electrocardiac parameters to an external device programmer 16, which then performs the discrimination. Discrimination by the pacer/CRT is preferred as that allows for prompt detection of possible arrhythmias but discrimination by an external system might be appropriate as well, at least for diagnostic purposes. Note also that other external systems might instead be used such as bedside monitors or the like. In some embodiments, the external system is directly networked with a centralized computing system, such as the HouseCall™ system or the Merlin@home—Merlin.Net systems of St. Jude Medical.

Summary of Discrimination Techniques Exploiting Proximal Electrode of LV Lead

Figure 2:
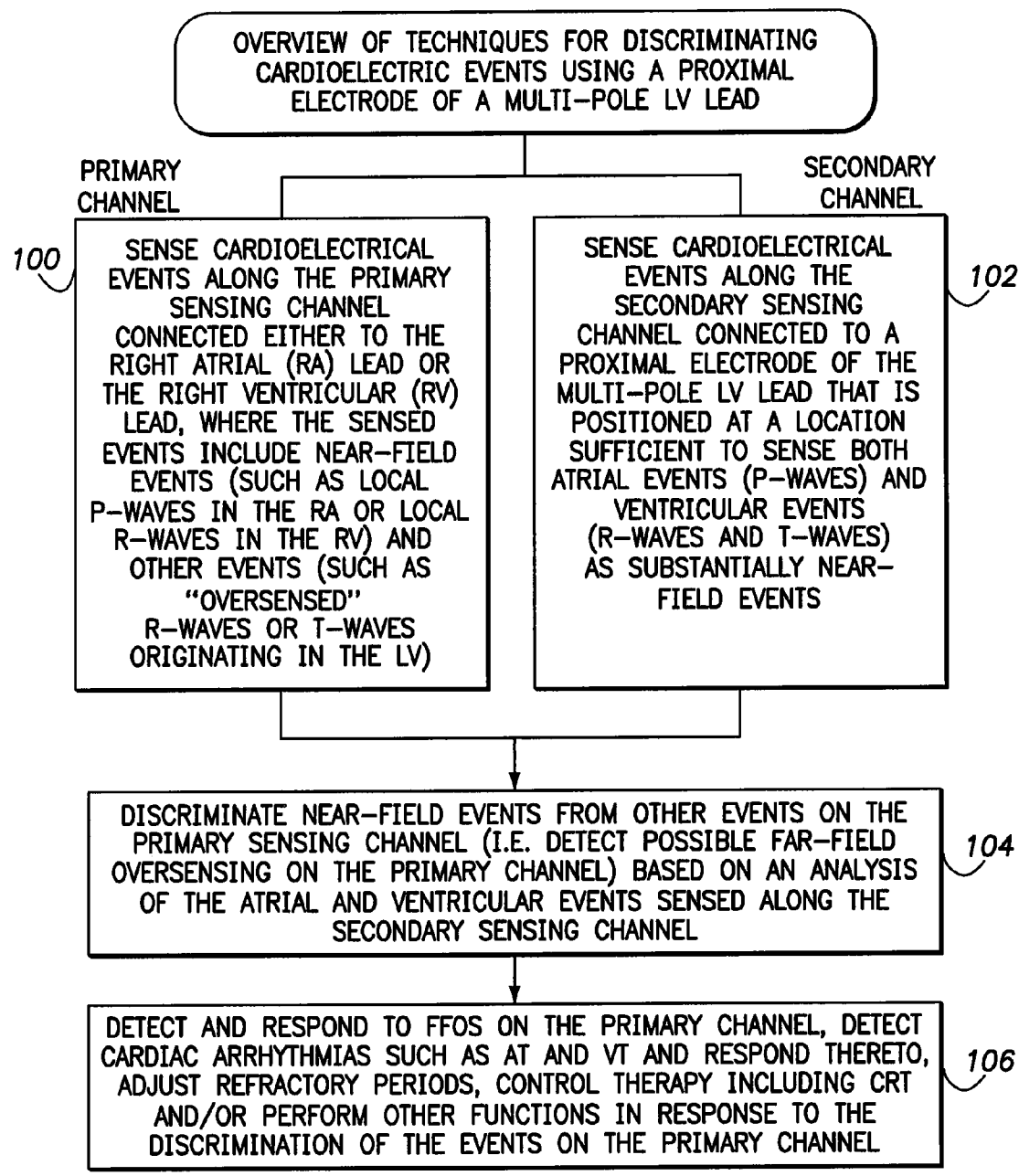
FIG. 2 summarizes the general technique for discriminating cardioelectric events that may be performed by the system of FIG. 1.

FIG. 2 broadly summarizes techniques exploited by the pacer/CRT of FIG. 1 (or other suitably-equipped systems) for discriminating cardioelectrical events using the proximal electrode of a multi-pole LV lead for use in detecting and responding to FFOS. In quad-pole examples, the proximal electrode of the LV lead is typically referred to as the P4 electrode but other designations may instead be used. In this example, at least two sensing channels are employed: a primary channel connected either to the RA or RV; and a secondary sensing channel connected to the proximal electrode of the LV lead. The designation of primary vs. secondary sensing channels is arbitrary. Moreover, it should be noted that state-of-the-art devices equipped with multipolar leads will often employ numerous additional sensing channels, including separate channels coupled to each of the electrodes of the LV lead. Only one primary channel and one secondary channel are presented in FIG. 2 so that pertinent features of the invention can be conveniently described without undue complication.

Beginning at step 100, the pacer/CRT senses cardioelectrical events along the primary sensing channel, which is connected either to the RA lead or the RV lead. The events sensed on the primary channel include near-field events (such as local P-waves in the RA or local R-waves in the RV) and other events (such as R-waves or T-waves originating in the LV). Concurrently, at step 102, the pacer/CRT also senses cardioelectrical events along the secondary sensing channel connected to the proximal electrode of the multi-pole LV lead, where the proximal electrode is positioned at a location sufficient to sense both atrial events (P-waves) and ventricular events (R-waves and T-waves) as substantially or approximately near-field events. For example, the proximal electrode might be implanted in or near the AV groove via the CS or great cardiac vain (GCV).

Figure 3:
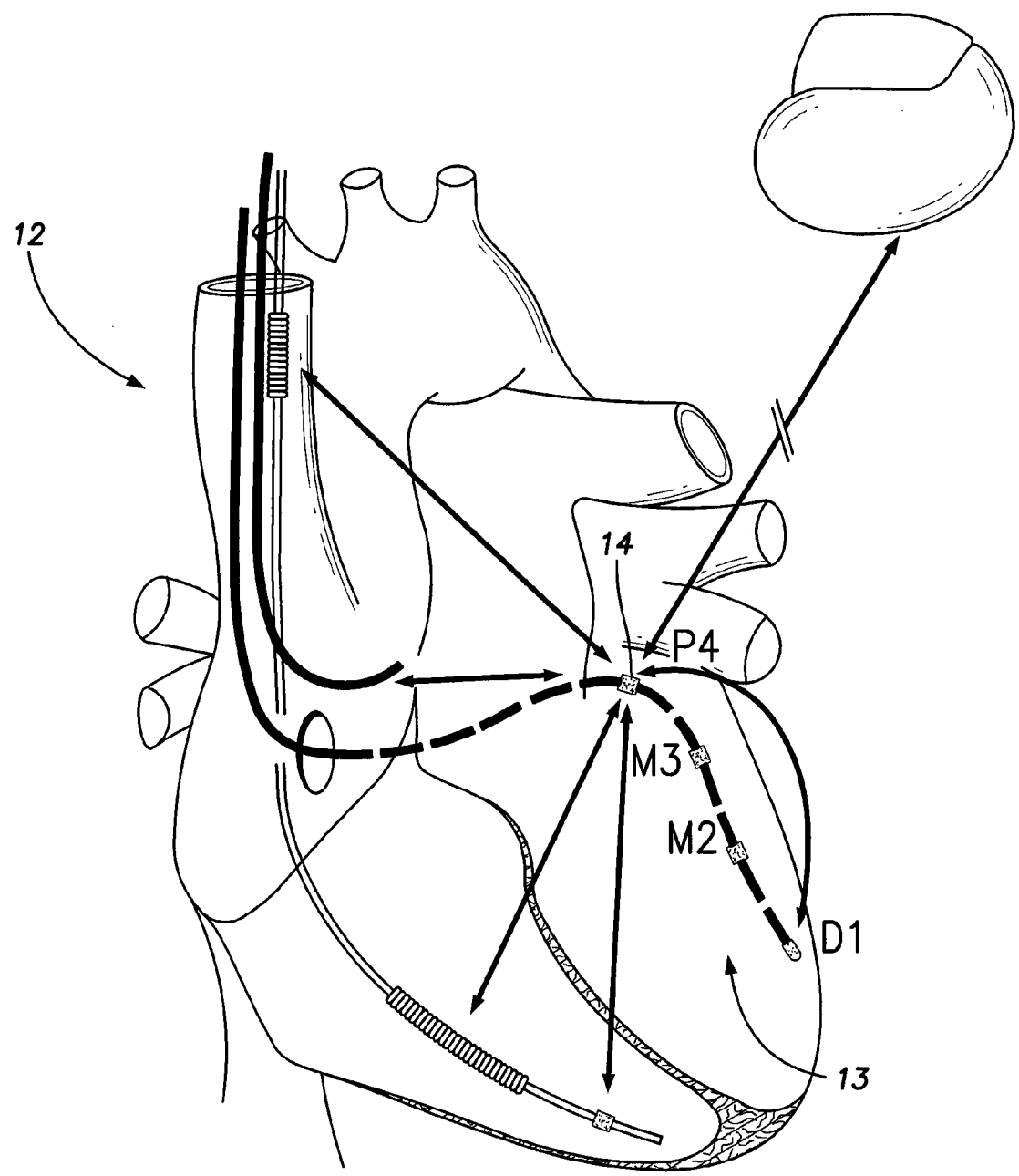
FIG. 3 illustrates a multi-polar LV lead and its implant location for use with the system of FIG. 1 wherein the proximal (P4) electrode of the LV lead is positioned in or near the AV groove of the heart via the CS or GCV.

FIG. 3 provides a stylized illustration of the heart of the patient showing the RA, RV and LV leads of lead system 12 in greater detail and, in particular, showing the four LV electrodes of the exemplary quad-pole LV lead, which are denoted from distal LV to proximal LV as: D1, M2, M3, and P4. As already noted, the P4 electrode is implanted (in this particular example) in or near the AV groove via the CS or GCV. The figure also shows various sensing vectors between the P4 electrode and other electrodes, particularly the RA ring, the RV ring, RV coil, SVC coil, and the LV D1 (tip) electrode, as well as the device housing electrode. The purpose of the various sensing vectors will be discussed below in connection with the detailed descriptions of the various exemplary embodiments.

With quad-pole leads such as the Quartet™ lead, the P4 proximal electrode lies in or near the AV groove in a substantial minority of patients and is positioned within the CS or GCV within about a quarter of the patients. Hence, the P4 electrode is often at a location sufficient to sense both atrial and ventricular events as near-field signals. Even if the P4 electrodes lies fully over LV tissue, it is almost always sufficiently close to the atria so that sensed signals will show atrial (A) potentials as well as ventricular (V) potentials as substantially near-field events. Insofar as the location of the AV groove is concerned, the atria of the heart are separated from the ventricles by the coronary sulcus (also called the coronary groove, auriculoventricular groove or AV groove). More specifically, the coronary sulcus is a surface groove encircling the heart that separates the atria from the ventricles. It contains the right coronary artery, the small cardiac vein, the coronary sinus, and the circumflex branch of the left coronary artery. Herein, the term "AV groove" is deemed to be generally equivalent to "coronary sulcus", "coronary groove" or "auriculoventricular groove."

Note that the particular locations of the implanted components shown in FIG. 3 are merely illustrative and may not necessarily correspond to actual implant locations. Also, although the descriptions herein use the Quartet™ lead as an exemplary component of the invention, it should be understood that any suitable lead could instead be used so long as it has at least one suitable electrode implanted at a location sufficient to sense both atrial and ventricular activation as substantially near-field signals. For most patients, a location in or near the AV groove via the CS or GCV should be sufficient but clinicians might identify other suitable implant locations.

Figure 4:
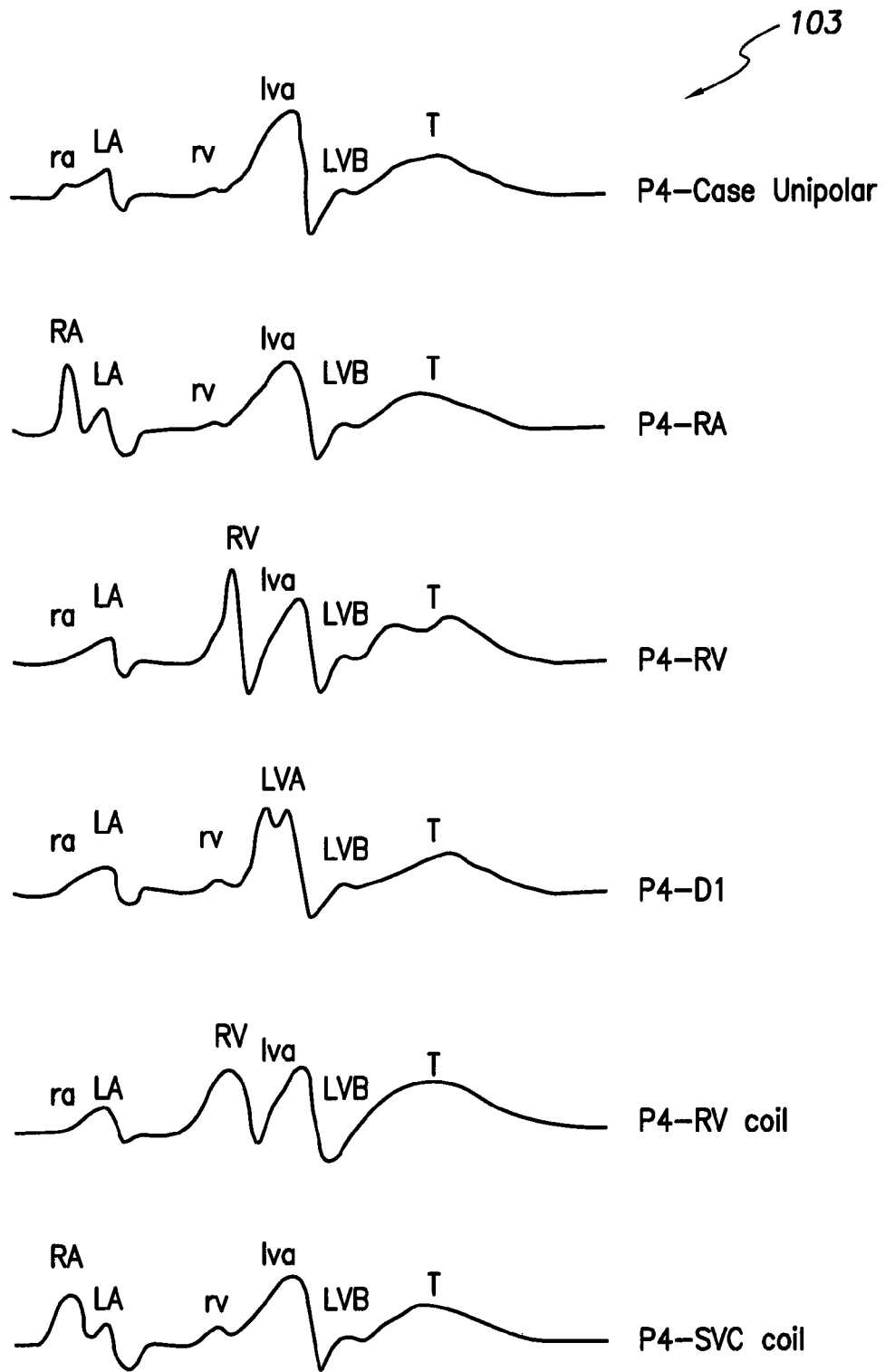
FIG. 4 presents IEGM traces illustrating exemplary signals sensed using the P4 electrode for use by the discrimination technique of FIG. 2.

FIG. 4 provides exemplary IEGM signal traces that might be sensed using the P4 electrode of a quad-pole lead along each of the six vectors illustrated in FIG. 3 for a patient with healthy conduction. More specifically, IEGM traces 103 corresponding to the following six exemplary vectors are shown:

1. P4 to Case (unipolar)
2. P4 to RA ring
3. P4 to RV ring
4. P4 to D1
5. P4 to RV coil
6. P4 to SVC coil One or more of these vectors are used as the aforementioned secondary sense channel for sensing signals at step 102 of FIG. 2. Based on the lead location in a given patient, the clinician (or suitable processing logic within the device or within an external system) selects one or two of these vectors that have substantial atrial and ventricular potentials. Within the figure, letters indicate particular cardiac events (with lower case indicating far-field ventricular events): RA, right atrial activation; LA, left atrial activation; RV, right ventricular activation; LVA, left ventricular apical activation; LVB, left ventricular basal activation; T, ventricular repolarization. Any of these vectors employing the P4 electrode will have near-field left atrial and basal left ventricular activation and hence will allow for sensing both atrial and ventricular signals as substantially or approximately near-field events. Note that choosing the P4 electrode as the cathode means those activations will likely manifest with steep positive slopes on the IEGM. Depending on the choice of anode, other activation events may appear as near-field events (with a steep slope) or as far-field events (with less steep deflection in either direction). Note also that positive deflection indicates activation is traveling toward the cathode and/or away from the anode. In the healthy conduction as shown, there is typically little doubt about what events correspond to any given deflection. However, in diseased myocardium with slowed conduction, ischemia or other anatomic and functional issues, the timing of various activation and repolarization events can fall into windows resulting in ambiguous interpretation from the IEGM, which the discrimination techniques of the present invention address.

Returning to FIG. 2, at step 104, the pacer/CRT discriminates near-field events from other events on the primary sensing channel based on an analysis of the atrial and ventricular events sensed along the secondary sensing channel connected to the proximal electrode of the LV lead. Exemplary techniques for performing the discrimination using templates will be described below. At step 106, the pacer/CRT detects and responds to FFOS, detects cardiac tachyarrhythmias such as AT and VT and responds thereto, adjusts atrial and/or ventricular refractory periods, controls therapy including CRT and/or performs other functions in response to the discrimination of the events on the primary channel.

These general techniques will now be described in more detail with reference to various illustrative examples.

Exemplary Techniques for Discriminating Events on an RA Sensing Channel

Figure 5:
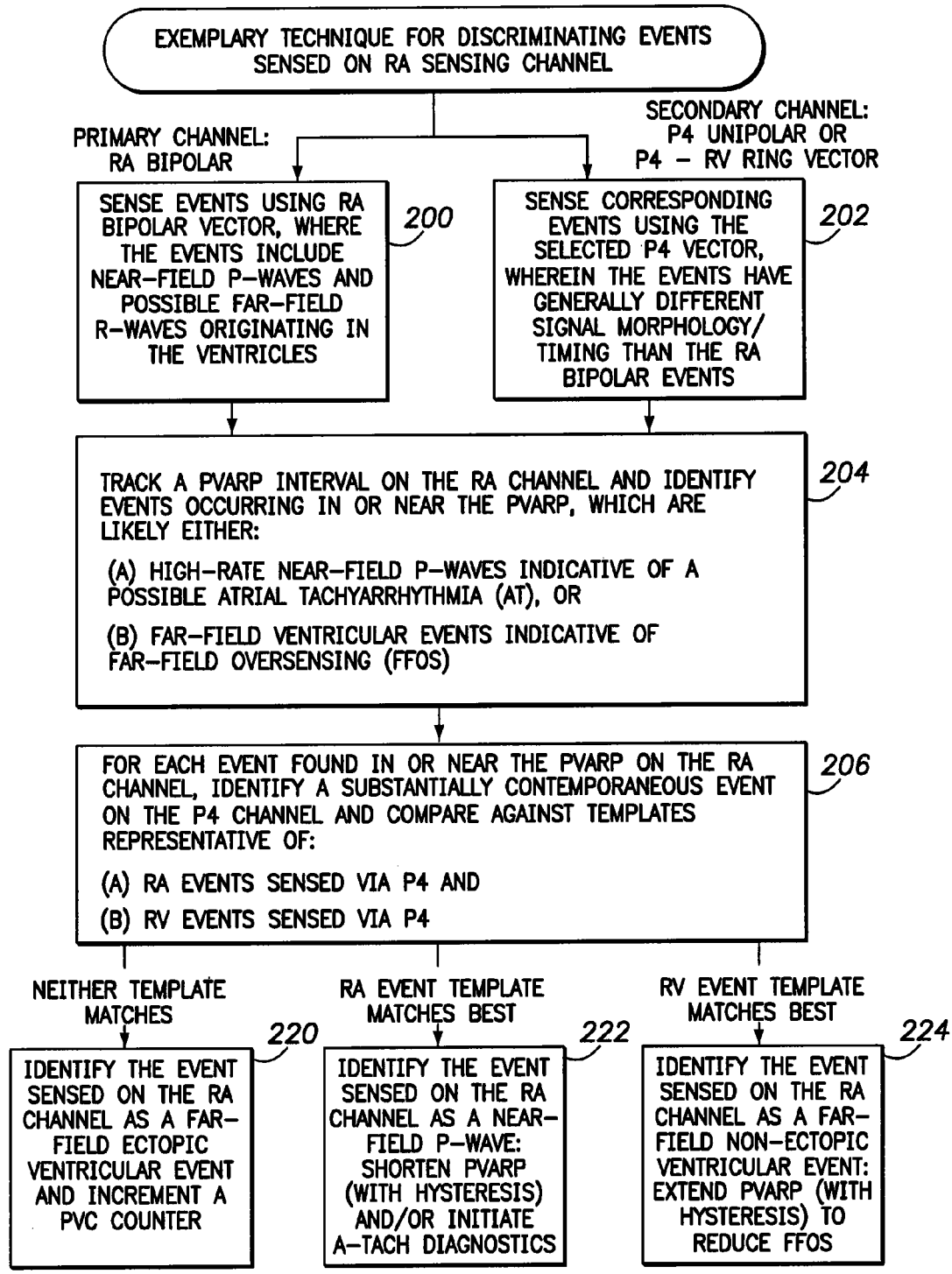
FIG. 5 is a flowchart illustrating a first exemplary discrimination technique for use with the general method of FIG. 2, wherein near-field RA events are discriminated from far-field ventricular events.
Figure 6:
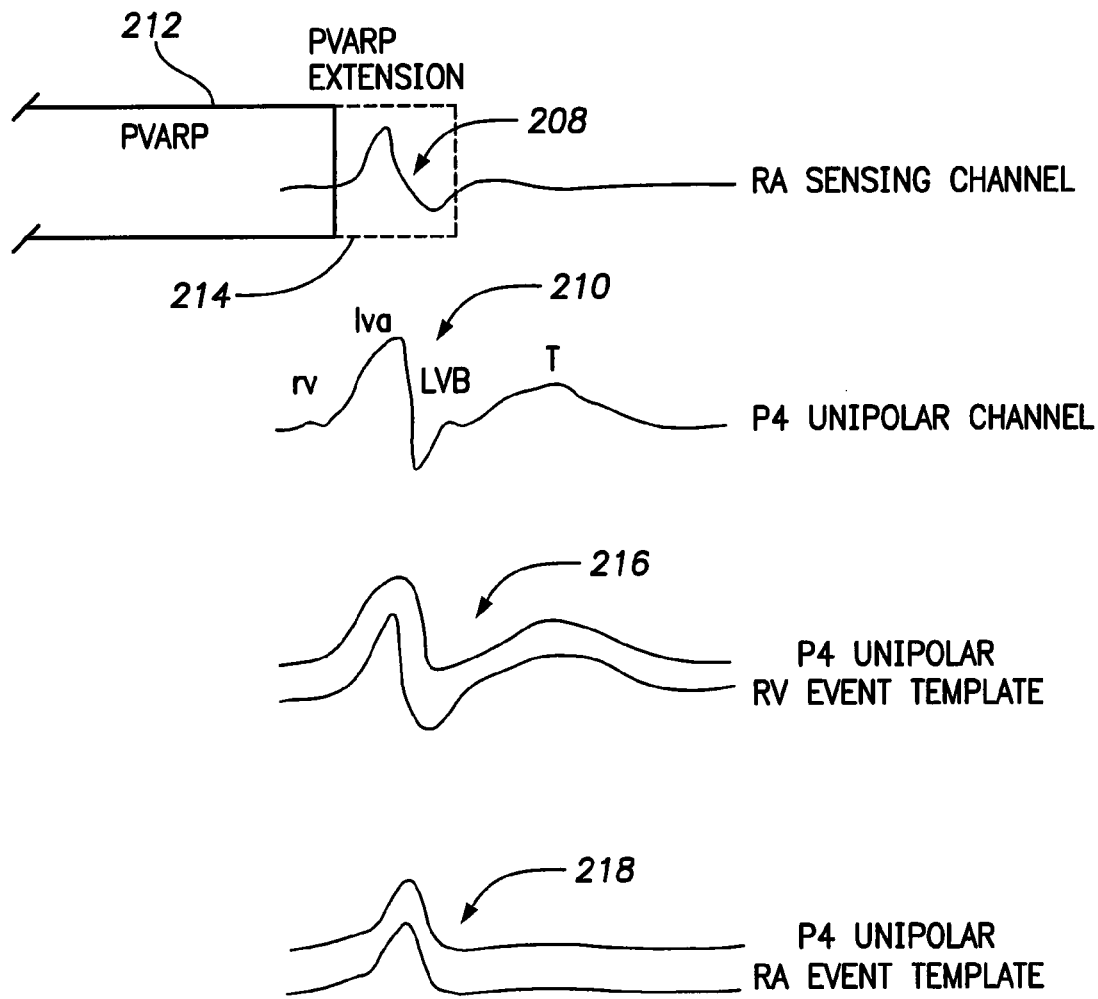
FIG. 6 presents IEGM traces illustrating exemplary signals sensed using the RA lead and using the P4 electrode for use by the discrimination technique of FIG. 5, as well as exemplary event discrimination templates.
Figure 7:
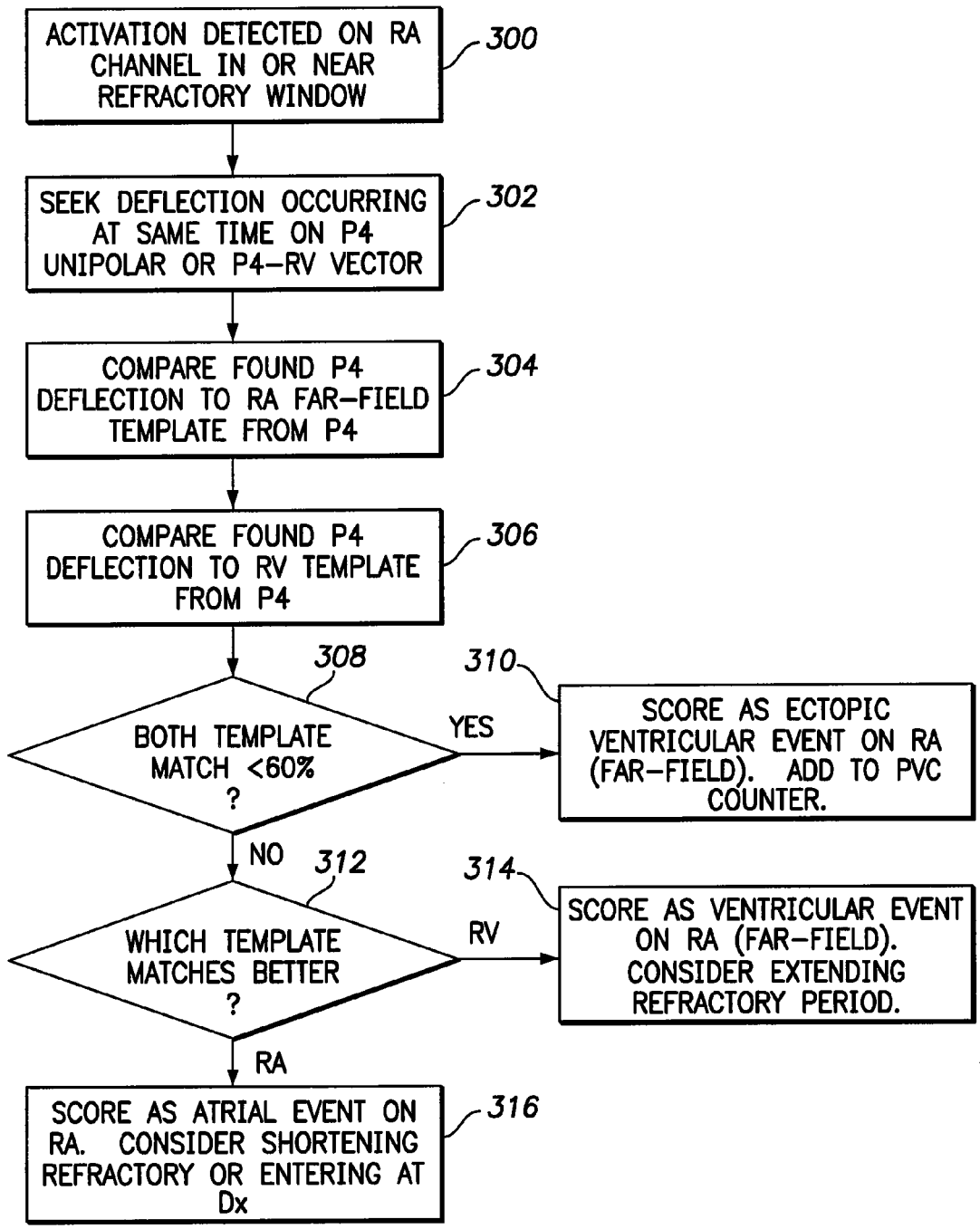
FIG. 7 is an alternative representation of the discrimination technique of FIG. 5 wherein near-field RA events are discriminated from far-field ventricular events.

FIGS. 5-7 illustrate discrimination techniques where the primary sensing channel is an RA bipolar channel. The multipolar lead in this example is a quad-pole lead and the secondary sensing channel is either a P4 unipolar channel or a P4-RV ring channel. The clinician might select other P4 channels for use as the secondary sensing channel, if deemed to be sufficient based on a review of the atrial and ventricular signals sensed thereon.

With this configuration, the techniques of FIGS. 5-7 are generally directed to discriminating near-field P-waves from far-field R-waves appearing on the RA sense channel. In this regard, far-field R-waves may occur on the RA channel if the PVAB or PVARP are set too short and is more likely if there is prolonged conduction from the RV sense to the bulk of ventricular myocardium of the LV. However, extending refractory intervals to cover possible far-field R-waves increases the chance of missing true P-waves that should be tracked and/or missing an atrial tachycardia such as sinus tachycardia (ST), atrial tachyarrhythmia (AT), atrial flutter (AFL), atrial fibrillation (AF) or SVT that would trigger mode switch or device therapy. For this case, the P4 unipolar or P4-RV ring are ideal vectors to aid in discrimination of atrial tachyarrhythmia versus far-field R-waves. The morphology of far-field right atrial activation on the P4 vector will be different from the morphology of R-waves on the same vector. Suitable methods of morphology discrimination (preferably template matching) can be used to categorize the IEGM deflection occurring in the time window of interest, as being more likely atrial or more likely ventricular activation based on which match is closer to the beat of interest in view of known P4 vector morphology. If the template matches RA far-field activation, the device scores the detection on the RA channel as an atrial activation; whereas if the template matches RV near- or far-field activation, the device ignores or rejects the deflection on the RA sense channel.

Now considering the technique of FIG. 5 in greater detail, beginning at step 200 the pacer/CRT senses events using RA bipolar vector, including near-field P-waves originating in the atria and possible R-waves originating in the ventricles. Concurrently, at step 202, the pacer/CRT senses corresponding events using the selected P4 vector, wherein the events have generally different signal morphology/timing than the RA bipolar events. At step 204, the pacer/CRT tracks a PVARP interval on the RA channel and identifies events occurring in or near the PVARP, which are, likely either: (a) high-rate near-field P-waves indicative of a possible atrial tachyarrhythmia (AT), or (b) far-field ventricular events indicative of FFOS. To detect events that are "near" the PVARP, the device can define an interval that extends somewhat beyond the normal PVARP. Any events detected within the extended interval are then deemed to be "near" the PVARP. Depending upon the particular embodiment, the extended interval might be defined to extend, e.g., 10% beyond the PVARP. At step 206, for each event found in or near the PVARP on the RA channel, the pacer/CRT identifies a substantially contemporaneous event on the P4 channel and compares it against templates representative of: (a) RA events sensed via P4 and (b) RV events sensed via P4.

FIG. 6 illustrates an exemplary event 208 sensed on the RA sensing channel and a corresponding event 210 sensed on the P4 channel. As can be seen, the events occur substantially contemporaneously to one another but have somewhat different shapes since the P4 channel senses ventricular signals more strongly than the RA sensing channel. To quantify whether any two events are "substantially contemporaneous," the pacer/CRT may compare the relative timing of the deflections to determine if they both occur within some predefined window. If so, the events are deemed to be substantially contemporaneous. FIG. 6 also illustrates a PVARP 212, as well as a PVARP extension 214 used to detect events "near" the PVARP. Since event 208 was sensed near the PVARP, it might be a high rate atrial event indicative of a possible atrial tachycardia or it might be a far-field R-wave. To distinguish therebetween, the device employs a pair of predetermined templates 216 and 218, wherein template 216 is representative of the shape of R-waves sensed via P4 and template 218 is representative of the shape of P-waves sensed via P4.

The templates may be determined by the clinician during a follow-up session following device implant and then stored in the memory of the pacer/CRT (and then adjusted as needed using techniques discussed below). In this particular example, the templates each include upper and lower signal "envelopes" and an event is deemed to match the template if the shape of the event fits between the upper and lower envelopes within some predetermined degree of precision. Another advantageous template matching method is one that disregards baseline values and normalizes the amplitude, and then rather than using upper and lower envelopes, computes the cross-correlation between template and measured signal, comparing the cross-correlation value to a predetermined threshold (such as 0.80). Other template forms may instead be used and otherwise conventional template matching techniques may be exploited. In some examples, different templates can be used depending upon patient posture or other factors that might affect the morphology of the IEGM signals.

See, also, the template matching techniques described in U.S. Pat. No. 6,516,225 of Florio, entitled "System and Method for Distinguishing Electrical Events Originating in the Atria from Far-Field Electrical Events Originating in the Ventricles as Detected by an Implantable Medical Device." In any case, event 210 sensed on the P4 channel is compared by the device against templates 216 and 218 to determine whether one or both (or neither) of the templates match.

Returning to FIG. 5, if neither of the templates match, then at step 220 the pacer/CRT identifies or "scores" the event sensed on the RA channel as a far-field ectopic ventricular event (i.e. an abnormal R-wave) and takes appropriate action, such as by incrementing a PVC counter so the device can track PVCs are respond if too many are detected. Assuming, however, that at least one of the two templates matches, the pacer/CRT determines which of the two templates matches better than the other. If the RA event template matches better than the RV template, then at step 222 the pacer/CRT identifies or scores the event sensed on the RA channel as a high rate near-field P-wave and responds accordingly, such as by shortening the PVARP to detect more high rate P-waves that might be obscured by the PVARP. Dynamic adjustment of the PVARP may exploit hysteresis, as discussed below. Additionally or alternatively, the device may initiate AT diagnostics at step 222. That is, predetermined procedures may be performed by the device in response to a possible AT, which serve to confirm the presence of AT and, assuming it is confirmed, to then deliver appropriate therapy if warranted. See, also, the therapeutic techniques discussed in the following documents: U.S. Pat. No. 7,826,899 to Ryu et al., entitled "Neurostimulation and Neurosensing Techniques to Optimize Atrial Anti-Tachycardia Pacing for Termination of Atrial Tachyarrhythmias" and U.S. Pat. No. 7,783,352 also to Ryu et al., entitled "Optimizing Anti-Tachycardia Pacing for Terminating Atrial Fibrillation." On the other hand, if the RV event template matches better than the RA template, then at step 224 the pacer/CRT identifies or scores the event sensed on the RA channel as a far-field non-ectopic ventricular event (i.e. a normal R-wave) and responds accordingly, such as by extending the PVARP to reduce further FFOS.

Hence, in addition to providing for detection of FFOS, the technique of FIG. 5 also provides for dynamic adjustment of PVARP intervals. For example, whenever a questionable event is scored as an atrial event by using the P4 electrode, PVARP is shortened by 5-10 ms, while when an event is scored as far-field R wave on the RA channel by using the P4 electrode, the PVARP is lengthened by 5-10 ms. The managing clinician can set boundaries as to how long or short this variable PVARP can become and may also choose to enable a "counter" such that it takes between one and eight such P4-scored detections within a specified time (for example in a 15-minute window) before PVARP will be changed. Further, dynamic PVARP hysteresis is possible by having a different number of required cycles to shorten PVARP versus that to extend PVARP. As noted above, enabling dynamic PVARP and dynamic PVARP hysteresis is important in patients with hypertrophic or dilated hearts (i.e. patients likely to exhibit larger far-field R waves) who may also be predisposed to atrial tachyarrhythmias. In any case, the amount by which the PVARP is adjusted during each iteration, the total range of any such adjustment, and whether PVARP hysteresis is employed can be pre-set or programmable, as specified by the clinician.

FIG. 7 provides an alternative flow chart illustrating the method of FIG. 5, which provides some additional details. Many of the steps are similar to those of FIG. 5 and hence will not be described in detail again. Beginning at step 300, the implanted device detects activation on the RA channel in or near a refractory window (such as the PVARP). At step 302, the device seeks an eflection occurring at about the same time on the P4 unipolar or P4-RV vectors.

At step 304, the device compares the deflection found on P4 to an RA far-field template (as sensed from P4). At step 306, the device compares the deflection found on P4 to an RV template (as sensed from P4). If neither template matches by at least 60% (or some other suitable percentage) at step 308, the device scores the event on the RA channel as a far-field ventricular ectopic event and increments the PVC counter at step 310. Otherwise, the device determines which template matches better. If the RV template matches better than the RA template at step 312, the device at step 314 scores the event on the RA channel as a normal far-field ventricular event and considers extending the refractory period. (This determination may be made, for example, based on the current duration of the refractory period and other factors). If the RA template matches better than the RV template, then at step 316 the device scores the event as an atrial event and considers shortening the refractory period and/or entering AT diagnostics.

Note that, where appropriate, the techniques of FIGS. 5-7 can be supplemented by other discrimination techniques or other atrial arrhythmia detection techniques. See, for example, techniques discussed in the following documents: U.S. Pat. No. 7,076,300 to Kroll et al., entitled "Implantable Cardiac Stimulation Device and Method that Discriminates between and Treats Atrial Tachycardia and Atrial Fibrillation"; U.S. Pat. No. 6,671,548 to Mouchawar et al., entitled "Implantable Stimulation Device and Method for Discrimination Atrial and Ventricular Arrhythmias"; and in U.S. Pat. No. 7,813,791 to Gill et al., entitled "Systems and Methods for Employing an FFT to Distinguish R-waves from T-waves using an Implantable Medical Device." See also, U.S. patent application Ser. No. 11/841,243 of Gill et al., filed Aug. 20, 2007, entitled "Systems and Methods for Employing an FFT to Detect Atrial Fibrillation Using an Implantable Medical Device."

Exemplary Techniques for Discriminating Events on an RV Sensing Channel

Figures 1, 8:
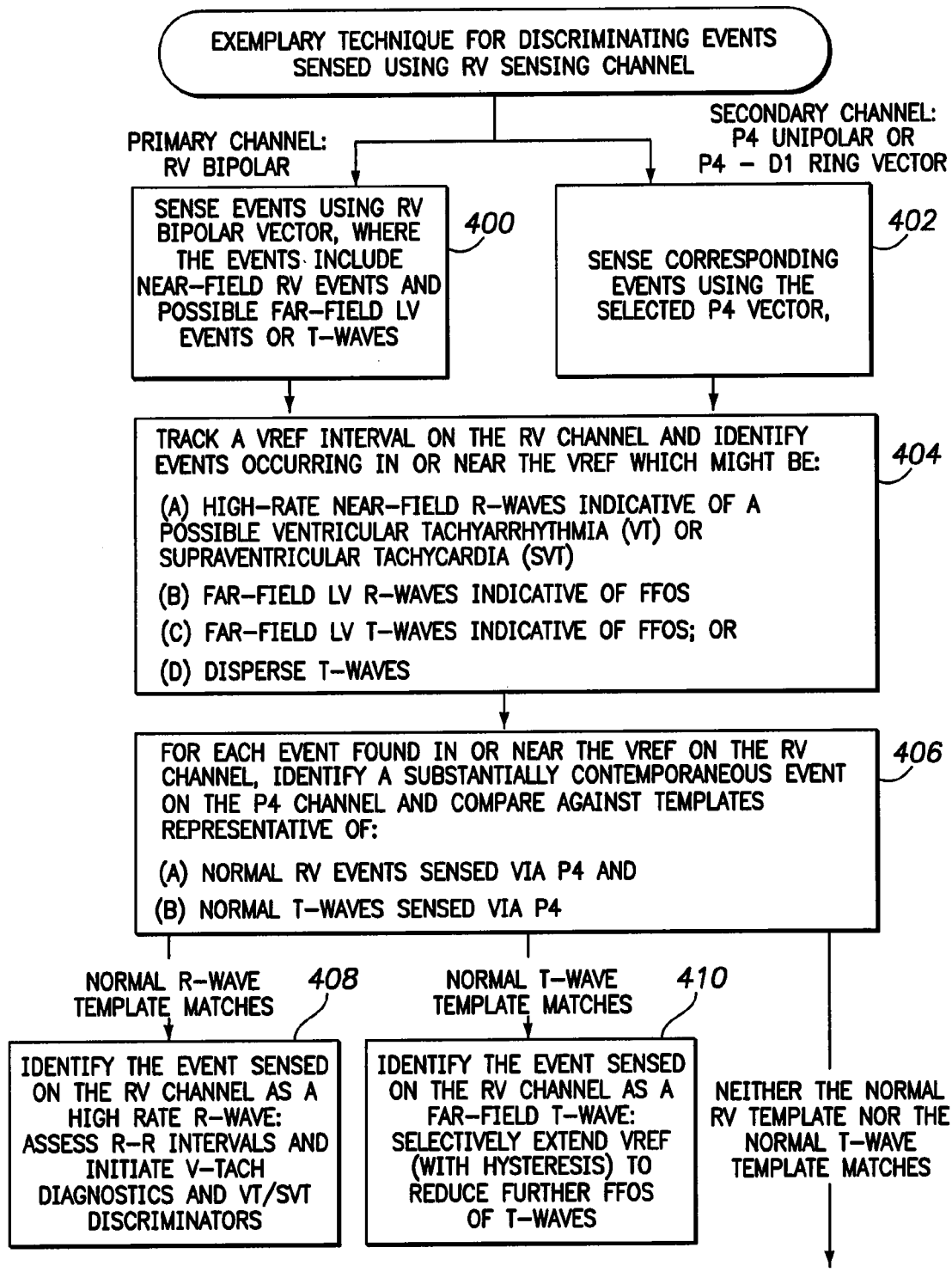
FIG. 8 is a flowchart illustrating a second exemplary discrimination technique for use with the general method of FIG. 2, wherein near-field RV events are discriminated from other ventricular events.
Figures 2, 8:
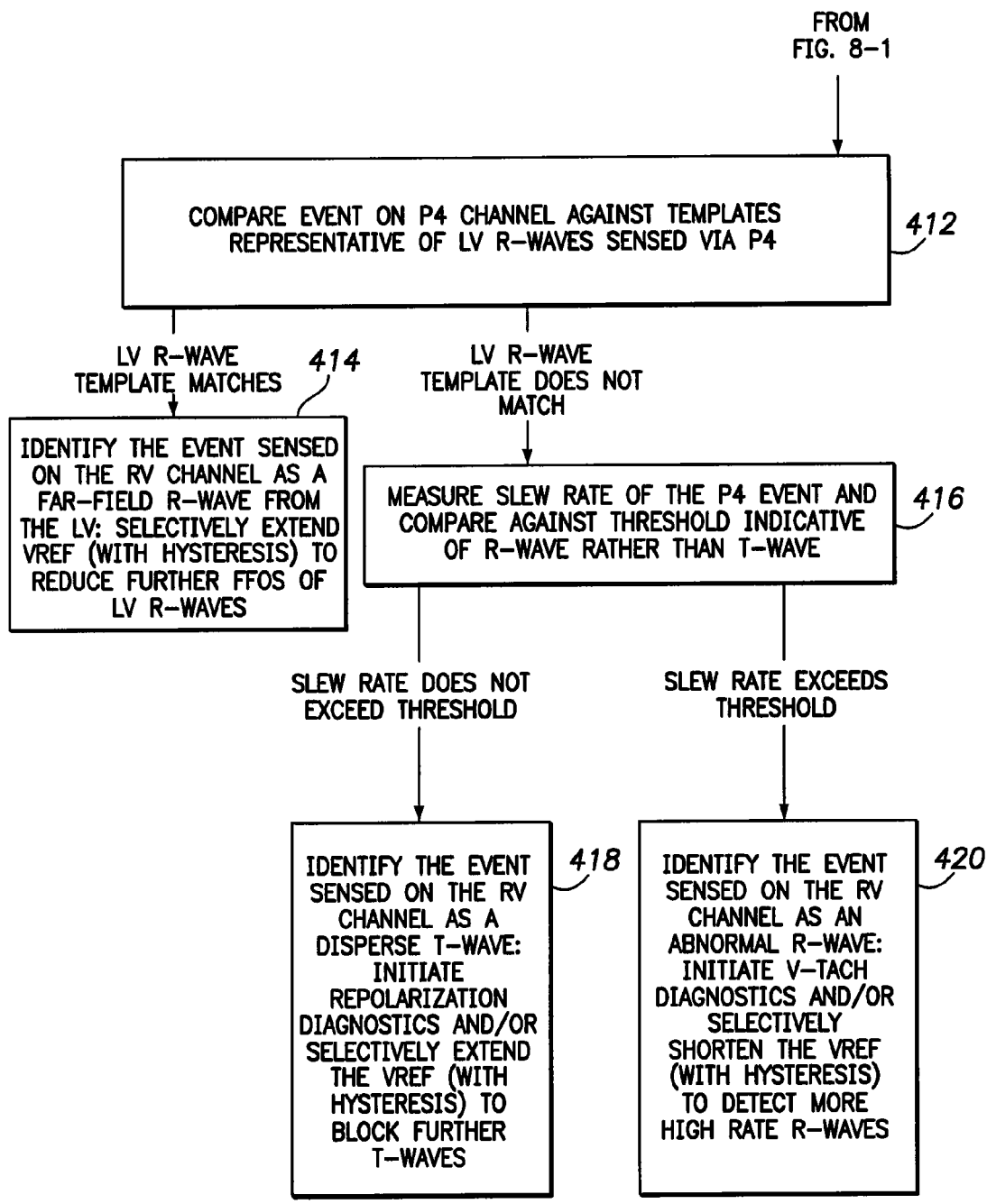
Figure 9:
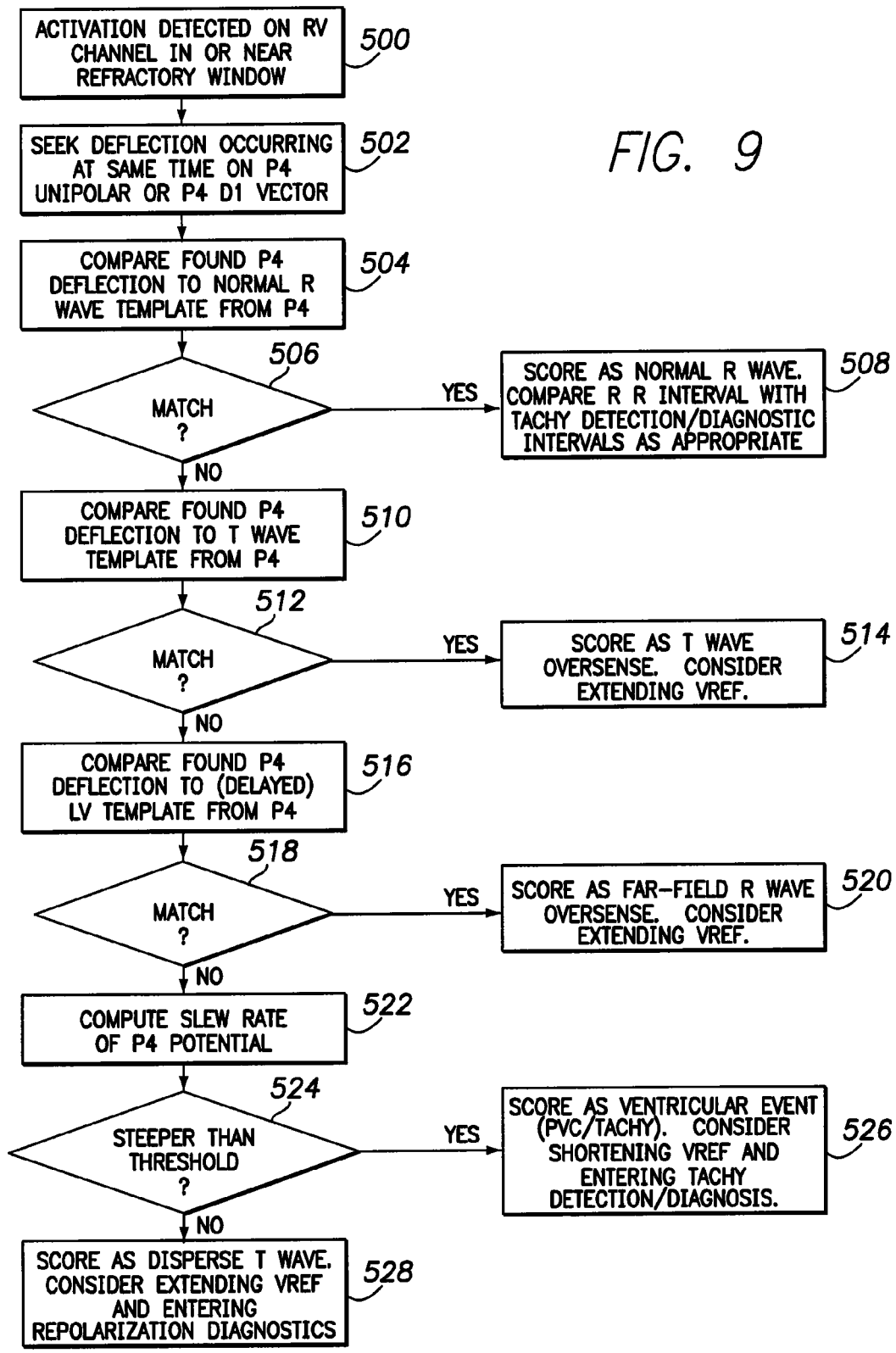
FIG. 9 is an alternative representation of the discrimination technique of FIG. 8 wherein near-field RV events are discriminated from other ventricular events.

FIGS. 8-9 illustrate examples where the primary sensing channel is an RV bipolar channel, i.e. the techniques operate to detect and respond to FFOS in the RV including T-wave oversensing, which can cause inappropriate detection/diagnosis of ventricular tachyarrhythmia. However, programming ventricular refractory periods (VREFs) longer to cover the T-wave increases the probability of missing a true ventricular tachyarrhythmia. For this case, the P4 unipolar vector or the P4-D1 sense vector is advantageous for contributing to discrimination of such questionable detection on the RV sense channel. Briefly, a deflection on the selected P4 vector occurring at or near the same time as the questionable detection on the RV sense channel is found. Morphology and slew rate of the P4 deflection is characterized. If the morphology matches T-wave morphology of known IEGM, then the event is discarded or rejected as a far-field T-wave. If the morphology matches near-field or far-field ventricular activation from previously characterized beats (for example, in the case of slow conduction from RV to LV such that the LV activation appears as far-field R wave on the RV sense channel), then the event is rejected as a far-field R-wave. However, if the morphology on P4 vector matches neither LV activation or T-wave, the slew rate is used to determine if the event is an ectopic activation (e.g. steeper than a predetermined threshold) or delayed repolarization (e.g. less steep than the threshold). The event can then be scored accordingly. To err on the side of safety during diagnoses of ventricular tachyarrhythmia, the slew rate criterion may be omitted and any non-matching P4 morphology is instead scored as PVC.

Note that the other ventricular electrodes may be utilized in similar discrimination procedures, for example by comparing the morphology and timing of D1-M2 electrogram and M3-P4 electrogram with prior similar (i.e. "like") morphologies and timings to determine whether an "extra" sensed signal is more likely to be ectopic ventricular activation or a delayed large amplitude repolarization. As with RA discrimination described above, it is possible to use the P4-detected events to drive lengthening or shortening ventricular refractory periods. For example, if the event is determined to be a far-field R-wave or T-wave, ventricular refractory can be extended; while if it is determined to be a PVC, the ventricular refractory may be shortened. Thus, dynamic VREF and dynamic VREF hysteresis are provided.

Turning now to FIG. 8, an exemplary RV discrimination procedure is set forth. Some of the steps are similar to those of the RA discrimination discussed above and hence will not be described again in detail. In this particular example, either the P4 unipolar channel or a P4-D1 channel is used as the secondary sensing channel. The clinician might select other P4 channels if deemed sufficient based on a review of the signals sensed thereon. Beginning at step 400, the pacer/CRT senses events using the RV bipolar vector where the events include near-field RV events and possible far-field LV R-waves and/or near-field or far-field T-waves. Concurrently at step 402, the pacer/CRT senses corresponding events using the selected P4 vector. At step 404, the pacer/CRT tracks a VREF interval on the RV channel and identifies events occurring in or near the VREF. These events might be: (a) high-rate near-field R-waves indicative of a possible VT or SVT; (b) far-field LV R-waves indicative of FFOS; (c) far-field LV T-waves indicative of FFOS; or (d) disperse T-waves, also indicative of oversensing. To detect events that are "near" the VREF, the device can define an interval that extends somewhat beyond the normal VREF (in the same manner as discussed above with reference to the PVARP). Insofar as the high-rate near-field R-waves are concerned, it is important to note that the device is comparing these events to "normal" R wave templates and, in some patients, "normal" implies that it is conducted from the atria through the AV node to the ventricles. Thus a "normal" R wave, or a signal matching the normal template, might be a conducted beat from the atria.

At step 406, for each event found in or near the VREF on the RV channel, the pacer/CRT identifies a substantially contemporaneous event on the P4 channel and initially compares the event against templates representative of: (a) normal RV events sensed via P4 and (b) normal T-waves sensed via P4. Templates of the type illustrated in FIG. 6 may be used, or other suitable templates may be employed. If the normal R-wave template matches, the device at step 408 identifies the event sensed on the RV channel as a high rate R-wave and then responds by, for example, assessing R-R intervals and initiating VT diagnostics and VT/SVT discriminators to confirm the VT or SVT. R-R interval measurement, and particularly R-R interval stability, represents one form of VT/SVT discrimination that is particularly good at identifying AF. However, there are others known in the art (such as A-V dissociation, sudden onset, and identifying in which chamber (A or V) the tachyarrhythmia initiates or terminates spontaneously or in response to extra stimulus) that may be employed. If the normal T-wave template matches, the device at step 410 instead identifies the event sensed on the RV channel as a far-field T-wave and then selectively extends the VREF to reduce further FFOS of T-waves. When dynamically adjusting the VREF, hysteresis of the type discussed above may be exploited. Note that if both the normal R-wave and the normal T-wave templates are found to match at step 406, the pacer/CRT selects between steps 408 and 410 based on which of the templates matches better. If neither of the two templates match, then at step 412 the pacer/CRT compares the event on the P4 channel against an additional template representative of LV R-waves sensed via P4 to determine if the event is a far-field R-wave originating in the LV. If the P4 event matches the LV R-wave template, the device identifies the event sensed on the RV channel as a far-field R-wave from the LV and responds by selectively extending VREF to reduce further FFOS of LV R-waves.

If the P4 event does not match the LV R-wave template, the device then examines the slew rate of the P4 event to distinguish between abnormal R-waves and disperse T-waves. That is, at step 416, the device measures the slew rate of the P4 event (i.e. the rate of change of the voltage of the P4 signal) and compares it against a predetermined threshold indicative of an R-wave rather than a T-wave. If the slew rate does not exceed the threshold (i.e. the slew rate is relatively slow), the device at step 418 identifies the event sensed on the RV channel as a disperse T-wave and then initiates repolarization diagnostics and/or selectively extends the VREF to block further T-waves. (Disperse T-waves occur when there is either a large difference in activation time across various regions of the heart, or larger spatial differences in activation-recovery interval, in both cases leading to a long time from the first cells repolarizing to the last cells repolarizing). Repolarization diagnostics can include various predetermined procedures that examine the morphology of the T-wave to assess its features. If the slew rate instead exceeds the threshold (i.e. the slew rate is relatively fast), the device at step 420 identifies the event sensed on the RV channel as an abnormal R-wave and initiates VT diagnostics and/or selectively shortens the VREF to detect additional high rate R-waves that might have been obscured by the VREF.

FIG. 9 provides an alternative flow chart illustrating the method of FIG. 8, which provides some additional details. Beginning at step 500, the implanted device detects activation on the RV channel in or near a refractory window (such as the VREF). At step 502, the device seeks a deflection occurring at about the same time on the P4 unipolar or P4-D1 vectors. At step 504, the device compares the deflection to a normal R-wave template (as sensed from P4). If there is a match at step 506, the device scores or identifies the event at step 508 as a normal R-wave and compares R-R intervals with predetermined tachycardia detection/diagnostics intervals to detect or confirm a possible VT or SVT and to discriminate therebetween using VT/SVT discriminators (as discussed above in connection with step 408 of FIG. 6). Otherwise, at step 510, the device compares the P4 deflection to a T-wave template (as sensed from P4). If there is a match at step 512, then at step 514 the device scores the event as an oversensed T-wave and considers extending the VREF. (This determination may be made by the device based, for example, on the current duration of the VREF and other factors). If there is no match at step 512, then at step 516, the device compares the deflection found on the P4 channel to a delayed LV template from P4. The template is delayed to account for conduction delays from the LV. If there is a match at step 518, the device then scores the event as an oversensed far-field R-wave at step 520 and considers extending the VREF. If there is still no template match, the device then examines slew rates. That is, at step 522, the device computes or measures the slew rate of the P4 potential (of the event or deflection detected at step 502) and compares the slew rate to a predetermined threshold at step 524. If the slew rate exceeds the threshold, then at step 526 the device scores the event as a PVC or a tachycardiac ventricular event and considers shortening the VREF and/or entering VT detection/diagnosis. Finally, if the slew rate does not exceed the threshold, the device at step 528 scores the events as a disperse T-wave and considers extending the VREF and entering the aforementioned repolarization diagnostics.

Note that, where appropriate, the techniques of FIGS. 8-9 can be supplemented by other discrimination techniques or other ventricular arrhythmia detection techniques. See, for example, techniques discussed in: U.S. Pat. No. 7,447,540 of Nabutovsky et al., entitled "Systems and Methods for Detection of VT and VF from Remote Sensing Electrodes"; U.S. Patent Application 2009/0287268 also of Nabutovsky et al., entitled "Methods and Systems for Improved Arrhythmia Discrimination"; U.S. Pat. No. 7,274,961 to Kroll et al., entitled "Implantable Cardiac Stimulation Device and Method that Discriminates between and Treats Ventricular Tachycardia and Ventricular Fibrillation"; U.S. Pat. No. 7,398,123 to Levine, entitled "Methods and Devices for Reducing the Detection of Inappropriate Physiologic Signals to Reduce Misdiagnosis of Normal Rhythms as Tachyarrhythmias"; and U.S. Pat. No. 6,711,438 to McClure et al., entitled "Method and Apparatus for Blanking T-waves from Combipolar Atrial Cardiac Signals based on Expected T-wave Locations." See, also, U.S. Pat. Nos. 7,146,213; 7,158,829; 7,174,210; and 7,184,834 to Levine, entitled "Method and Apparatus for Improving Specificity of Tachycardia Detection Techniques in Dual-unipolar and Dual-Bipolar Implantable Cardiac Stimulation Systems."

Exemplary Techniques for Template Maintenance

Figure 10:
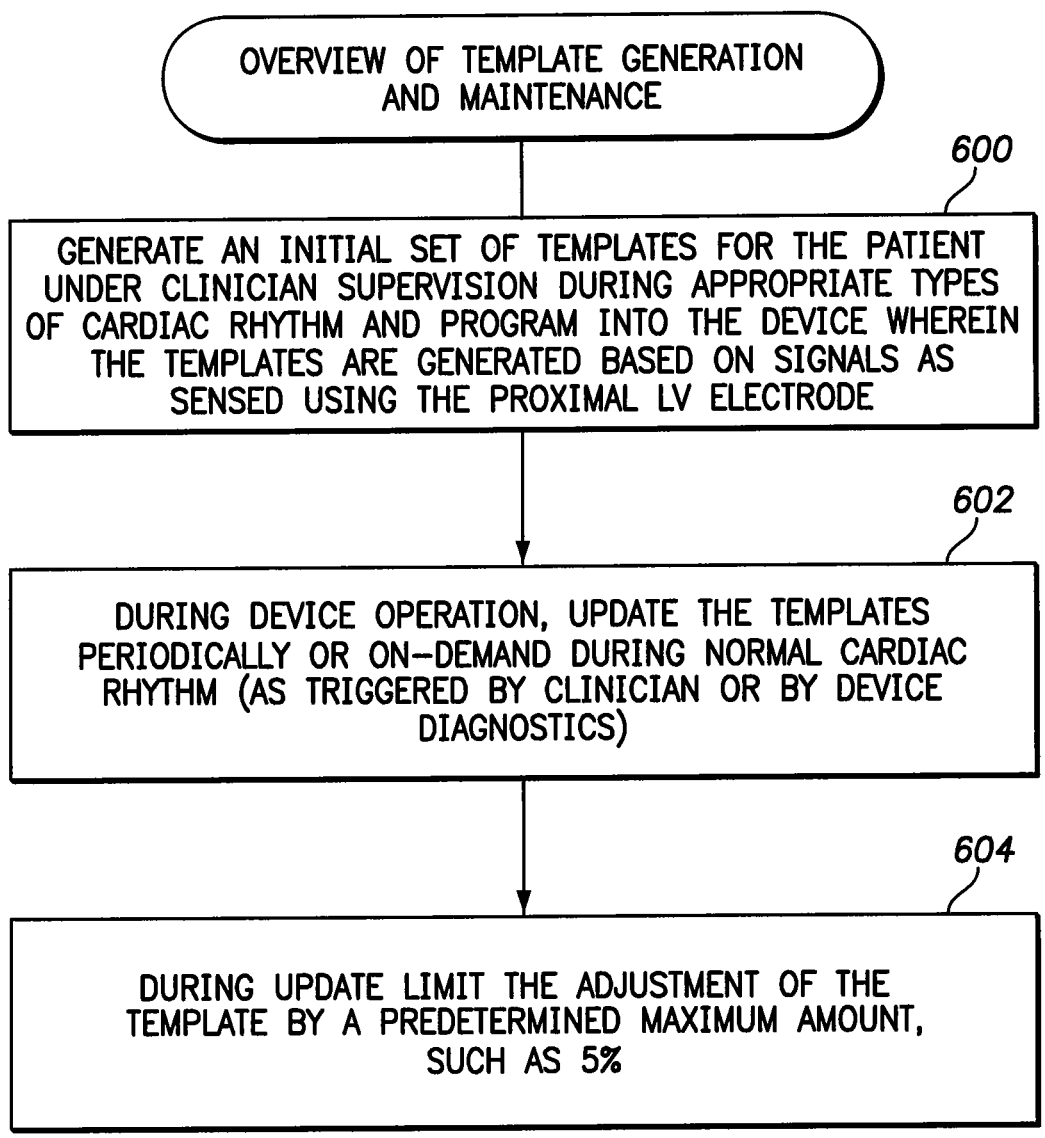
FIG. 10 summarizes techniques for use in generating and adjusting the templates used by the methods of FIGS. 4-9.

FIG. 10 broadly summarizes techniques that may be used to generate and update the aforementioned templates. Briefly, at step 600, the implantable device (or an external system such as a device programmer) generates an initial set of templates for the patient under clinician supervision during appropriate types of cardiac rhythm and programs the templates into the memory of the implanted device. The templates are generated based on signals as sensed using the proximal (P4) LV electrode. For example, to generate R-wave and T-wave templates for normal sinus rhythm, the device senses R-waves and T-waves via the P4 channel during normal sinus rhythm and records templates representative of the signal morphology as observed via the P4 channel. Likewise, to generate P-wave templates for normal sinus rhythm, the device senses P-waves via the P4 channel during normal sinus rhythm and records the templates. Different templates might be generated for different conditions that might affect signal morphology (such as different postures).

At step 602, during subsequent device operation, the templates are updated periodically or on-demand by the implanted device (or by an external system such as a bedside monitor) during normal cardiac rhythm. "On-demand" updating may be triggered by a clinician or by device diagnostics. For example, if too many false positives are detected by the device (which may arise due to changes in the morphology of the patient's IEGM), the device can update the templates to address the problem. Changes in signal morphology may arise due to use of prescription medications or due to changes in the heart (e.g., ischemia, infarction, or progression of heart disease). At step 604, during any update to the templates, the device preferably limits the magnitude of the adjustment by a predetermined maximum amount, such as 5%, so that the individual adjustments are not too great.

Although primarily described with respect to examples having a CRT with pacing capability (i.e. a CRT-P), other implantable medical devices may be equipped to exploit the techniques described herein such as CRT-D devices, as well as standalone pacemakers or ICDs. When exploited in a CRT, the device can exploit a wide variety of techniques to improve CRT capability. See, for example, the techniques discussed in: U.S. Published Patent Application 2010/0268059 of Ryu et al., entitled "Therapy Optimization via Multi-Dimensional Mapping" and U.S. Patent Application 2010/0152801 of Koh et al., entitled "Cardiac Resynchronization Therapy Optimization using Vector Measurements Obtained from Realtime Electrode Position Tracking." See, also, U.S. Patent Application No. 2008/0306567 of Park et al., entitled "System and Method for Improving CRT Response and Identifying Potential Non-Responders to CRT Therapy" and U.S. Pat. No. 7,653,436 of Schecter, entitled "Global Cardiac Performance."

For the sake of completeness, an exemplary pacer/CRT will now be described, which includes components for performing the functions and steps already described, as well as components for controlling CRT.

Exemplary Pacer/CRT

Figure 11:
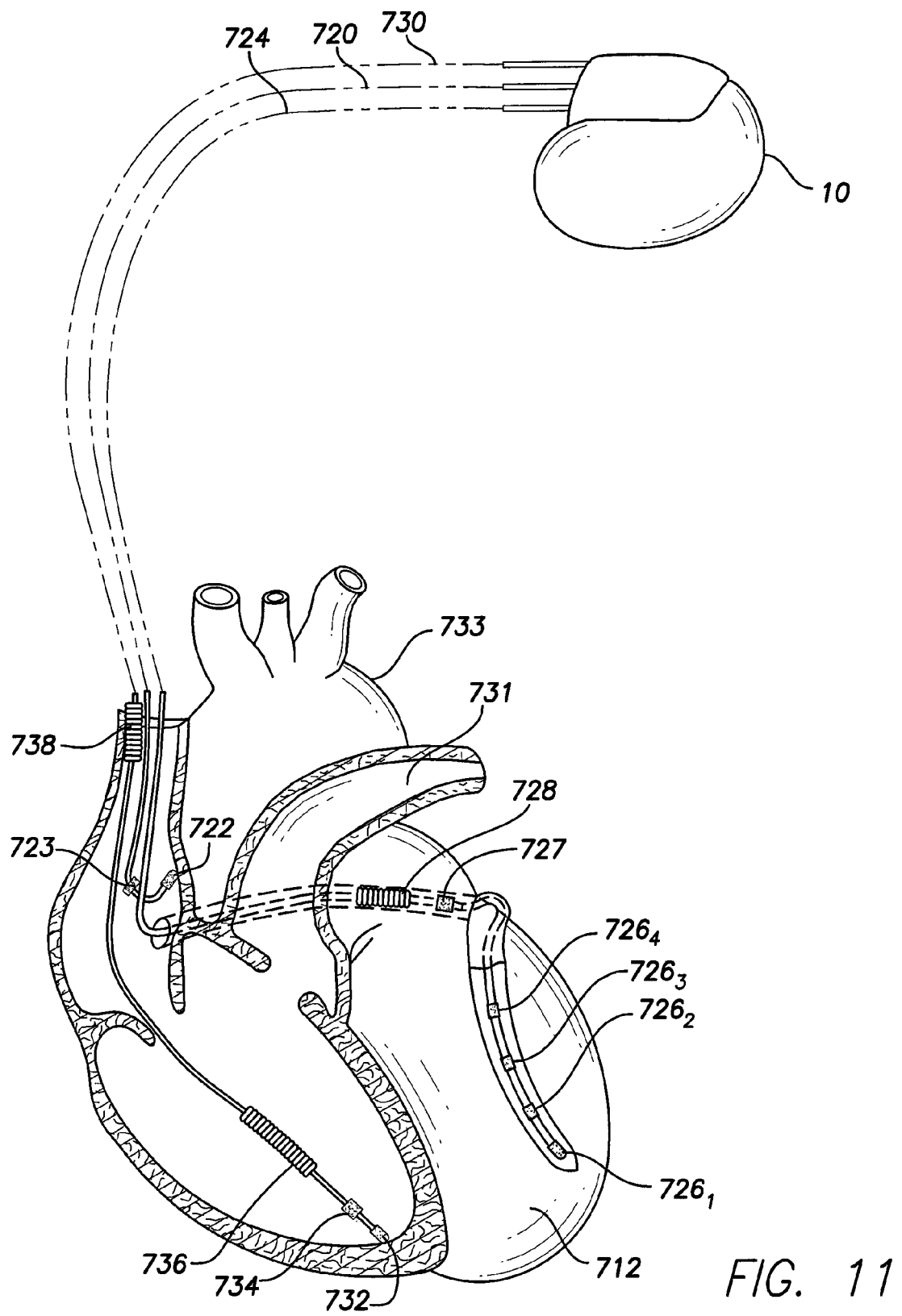
FIG. 11 is a simplified, partly cutaway view, illustrating the device of FIG. 1 along with at set of leads implanted in or on the heart of the patient.
Figure 12:
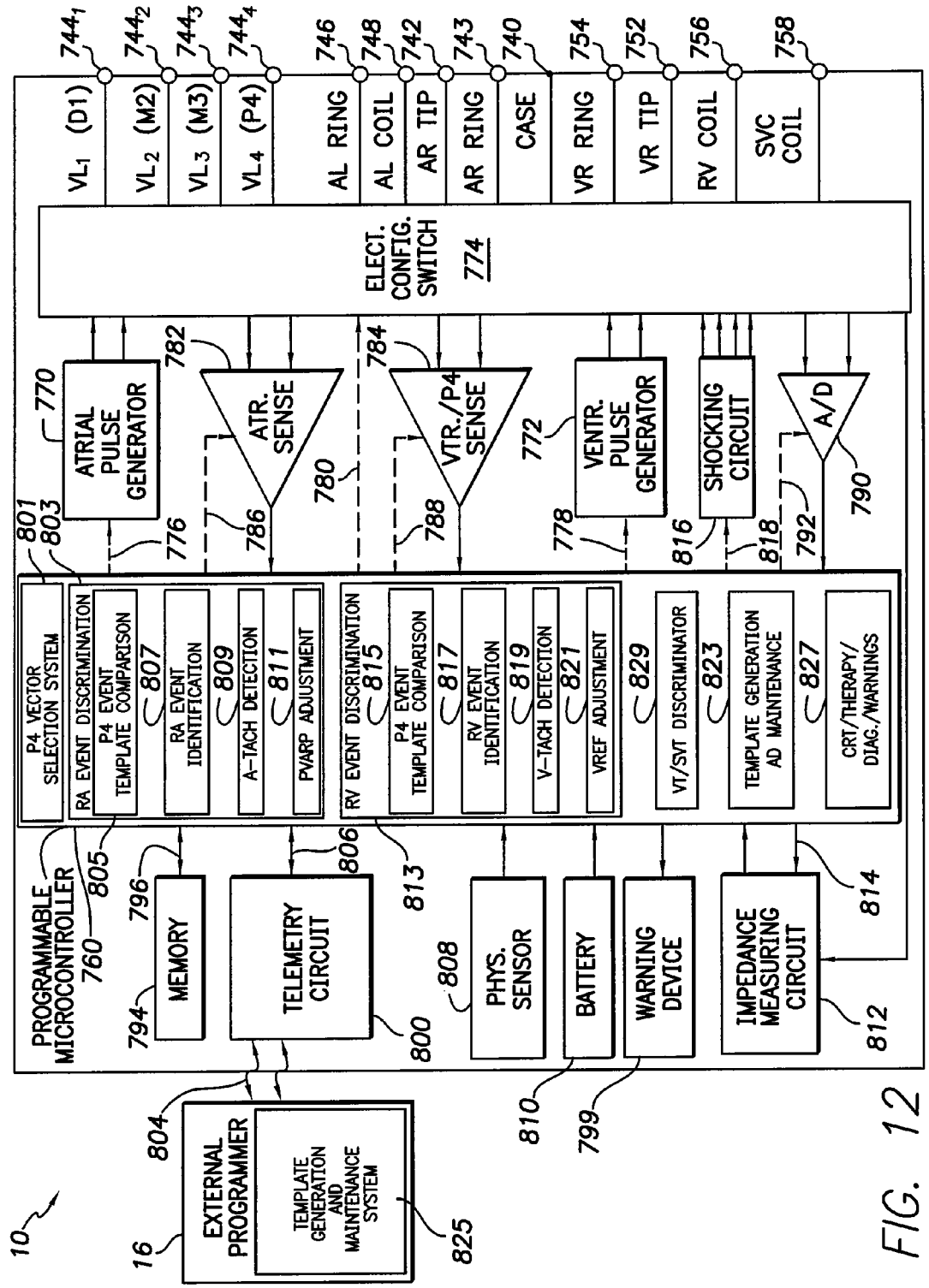
FIG. 12 is a functional block diagram of the pacer/CRT of FIG. 11, illustrating basic circuit elements that provide cardioversion, defibrillation and/or pacing stimulation in the heart and particularly illustrating components for performing the discrimination techniques of FIGS. 2-10.

With reference to FIGS. 11 and 12, a description of an exemplary pacer/CRT will now be provided. FIG. 11 provides a simplified block diagram of the pacer/CRT, which is a dual-chamber stimulation device capable of treating both fast and slow arrhythmias with stimulation therapy, including cardioversion, defibrillation, and pacing stimulation, and also capable of discriminating RA and RV events, as discussed above. To provide atrial chamber pacing stimulation and sensing, pacer/CRT 10 is shown in electrical communication with a heart 712 by way of a left atrial lead 720 having an atrial tip electrode 722 and an atrial ring electrode 723 implanted in the atrial appendage. Pacer/CRT 10 is also in electrical communication with the heart by way of a right ventricular lead 730 having, in this embodiment, a ventricular tip electrode 732, a right ventricular ring electrode 734, a right ventricular (RV) coil electrode 736, and a superior vena cava (SVC) coil electrode 738. Typically, the right ventricular lead 730 is transvenously inserted into the heart so as to place the RV coil electrode 736 in the right ventricular apex, and the SVC coil electrode 738 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/CRT 10 is coupled to a multi-pole LV lead 724 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, the exemplary LV lead 724 is designed to receive atrial and ventricular cardiac signals and to deliver left ventricular pacing therapy using a set of four left ventricular electrodes $726_1$ (D1), $726_2$ (M2), $726_3$ (M3), and $726_4$ (P4), left atrial pacing therapy using at least a left atrial ring electrode 727, and shocking therapy using at least a left atrial coil electrode 728. The $726_1$ LV electrode may also be referred to as a "tip" or "distal" LV electrode. The $726_4$ LV electrode may also be referred to as a "proximal" LV electrode. In other examples, more or fewer LV electrodes are provided. Although only three leads are shown in FIG. 11, it should also be understood that additional leads (with one or more pacing, sensing and/or shocking electrodes) might be used and/or additional electrodes might be provided on the leads already shown, such as additional electrodes on the RV lead. Also, note that the P4 electrode $726_4$ may be located in or near the AV groove as discussed above. The details of this configuration are not necessarily shown in this particular figure.

It is noted that, in practice, electrodes 726 are on the "left heart lead" and depending upon where the lead is implanted, in most patients, all four electrodes can be in LV but, in a substantial minority of patients, the P4 electrode is situated close to the LA (specifically in AV groove). As noted above, the P4 electrode is the electrode on which both atrial and ventricular activation is sensed as substantially near-field events (which can also be achieved even if the electrode is primarily on the LV instead of LA). On present commercially-available hardware, there is often no separate electrode 727. That is, the P4 electrode $726_4$ and the "left atrial ring electrode" 727 are one and the same. Hence, it should be understood that the "left atrial ring electrode" could instead be used as the P4 electrode, assuming it is suitably positioned at a location sufficient to sense both atrial and ventricular signals as substantially near-field events. Both electrodes are shown for the sake of completeness and generality.

A simplified block diagram of internal components of pacer/CRT 10 is shown in FIG. 12. While a particular pacer/CRT is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 740 for pacer/CRT 10, shown schematically in FIG. 12, is often referred to as the "can", "case" or "case electrode" and may be programmably selected to act as the return electrode for all "unipolar" modes. The housing 740 may further be used as a return electrode alone or in combination with one or more of the coil electrodes, 728, 736 and 738, for shocking purposes. The housing 740 further includes a connector (not shown) having a plurality of terminals, 742, 743, $744_1$-$744_4$, 746, 748, 752, 754, 756 and 758 (shown schematically and, for convenience, the names of the electrodes to which they are connected are shown next to the terminals). As such, to achieve right atrial sensing and pacing, the connector includes at least a right atrial tip terminal ($A_R$ TIP) 742 adapted for connection to the atrial tip electrode 722 and a right atrial ring ($A_R$ RING) electrode 743 adapted for connection to right atrial ring electrode 723. To achieve left chamber sensing, pacing and shocking, the connector includes a left ventricular tip terminal ($VL_1$ (D1)) $744_1$ and additional LV electrode terminals $744_2$-$744_4$ for the other LV electrodes of the LV lead.

The connector also includes a left atrial ring terminal ($A_L$ RING) 746 and a left atrial shocking terminal ($A_L$ COIL) 748, which are adapted for connection to the left atrial ring electrode 727 and the left atrial coil electrode 728, respectively. To support right chamber sensing, pacing and shocking, the connector further includes a right ventricular tip terminal ($V_R$ TIP) 752, a right ventricular ring terminal ($V_R$ RING) 754, a right ventricular shocking terminal (RV COIL) 756, and an SVC shocking terminal (SVC COIL) 758, which are adapted for connection to the right ventricular tip electrode 732, right ventricular ring electrode 734, the $V_R$ coil electrode 736, and the SVC coil electrode 738, respectively.

At the core of pacer/CRT 10 is a programmable microcontroller 760, which controls the various modes of stimulation therapy. As is well known in the art, the microcontroller 760 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 760 includes the ability to process or monitor input signals (data) as controlled by a program code stored in a designated block of memory. The details of the design and operation of the microcontroller 760 are not critical to the invention. Rather, any suitable microcontroller 760 may be used that carries out the functions described herein. The use of microprocessor-based control circuits for performing timing and data analysis functions are well known in the art.

As shown in FIG. 12, an atrial pulse generator 770 and a ventricular pulse generator 772 generate pacing stimulation pulses for delivery by the right atrial lead 720, the right ventricular lead 730, and/or the LV lead 724 via an electrode configuration switch 774. It is understood that in order to provide stimulation therapy in each of the four chambers of the heart, the atrial and ventricular pulse generators 770, 772 may include dedicated, independent pulse generators, multiplexed pulse generators or shared pulse generators. The pulse generators 770, 772, are controlled by the microcontroller 760 via appropriate control signals 776, 778 respectively, to trigger or inhibit the stimulation pulses.

The microcontroller 760 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 774 includes a plurality of switches for connecting the desired electrodes to the appropriate I/O circuits, thereby providing complete electrode programmability. Accordingly, the switch 774, in response to a control signal 780 from the microcontroller 760, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 782 and ventricular sensing circuits 784 may also be selectively coupled to the right atrial lead 720, LV lead 724, and the right ventricular lead 730, through the switch 774 for detecting the presence of cardiac activity in each of the four chambers of the heart. The ventricular sense circuit preferably accommodates at least one P4 sensing channel. Accordingly, the atrial and ventricular sensing circuits 782, 784 may include dedicated sense amplifiers, multiplexed amplifiers or shared amplifiers. The switch 774 determines the "sensing polarity" of the cardiac signal by selectively closing the appropriate switches, as is also known in the art. In this way, the clinician may program the sensing polarity independent of the stimulation polarity. Each sensing circuit 782, 784 preferably employs one or more low power, precision amplifiers with programmable gain and/or automatic gain control, bandpass filtering, and a threshold detection circuit, as known in the art, to selectively sense the cardiac signal of interest. The automatic gain control enables pacer/CRT 10 to deal effectively with the difficult problem of sensing the low amplitude signal characteristics of atrial or ventricular fibrillation. The outputs of the atrial and ventricular sensing circuits 782, 784 are connected to the microcontroller 760 which, in turn, are able to trigger or inhibit the atrial and ventricular pulse generators 770, 772 respectively, in a demand fashion in response to the absence or presence of cardiac activity in the appropriate chambers of the heart.

For arrhythmia detection, pacer/CRT 10 utilizes the atrial and ventricular sensing circuits 782, 784 to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 760 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 790. The data acquisition system 790 is configured to acquire intracardiac electrogram signals, convert the raw analog data into a digital signal, and store the digital signals for later processing and/or telemetric transmission to an external device 16. The data acquisition system 790 is coupled to the right atrial lead 720, the LV lead 724, and the right ventricular lead 730 through the switch 774 to sample cardiac signals across any pair of desired electrodes. The microcontroller 760 is further coupled to a memory 794 by a suitable data/address bus 796, wherein the programmable operating parameters used by the microcontroller 760 are stored and modified, as required, in order to customize the operation of pacer/CRT 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/CRT 10 may be non-invasively programmed into the memory 794 through a telemetry circuit 800 in telemetric communication with the external device 16, such as a programmer, transtelephonic transceiver or a diagnostic system analyzer. The telemetry circuit 800 is activated by the microcontroller by a control signal 806. The telemetry circuit 800 advantageously allows intracardiac electrograms and status information relating to the operation of pacer/CRT 8 (as contained in the microcontroller 760 or memory 794) to be sent to the external device 802 through an established communication link 804. Pacer/CRT 10 further includes an accelerometer or other physiologic sensor 808, commonly referred to as a "rate-responsive" sensor because it is typically used to adjust pacing stimulation rate according to the exercise state of the patient. However, the physiological sensor 808 may further be used to detect changes in cardiac output, changes in the physiological condition of the heart, or diurnal changes in activity (e.g., detecting sleep and wake states) and to detect arousal from sleep. Accordingly, the microcontroller 760 responds by adjusting the various pacing parameters (such as rate, AV delay, VV delay, etc.) at which the atrial and ventricular pulse generators, 770 and 772, generate stimulation pulses. While shown as being included within pacer/CRT 10, it is to be understood that the physiologic sensor 808 may also be external to pacer/CRT 10, yet still be implanted within or carried by the patient. A common type of rate responsive sensor is an activity sensor incorporating an accelerometer or a piezoelectric crystal, which is mounted within the housing 740 of pacer/CRT 10. Other types of physiologic sensors are also known, for example, sensors that sense the oxygen content of blood, respiration rate and/or minute ventilation, pH of blood, ventricular gradient, etc.

The pacer/CRT additionally includes a battery 810, which provides operating power to all of the circuits shown in FIG. 12. The battery 810 may vary depending on the capabilities of pacer/CRT 10. If the system only provides low voltage therapy, a lithium iodine or lithium copper fluoride cell typically may be utilized. For pacer/CRT 10, which employs shocking therapy, the battery 810 should be capable of operating at low current drains for long periods, and then be capable of providing high-current pulses (for capacitor charging) when the patient requires a shock pulse. The battery 810 should also have a predictable discharge characteristic so that elective replacement time can be detected. Accordingly, appropriate batteries are employed.

As further shown in FIG. 12, pacer/CRT 10 is shown as having an impedance measuring circuit 812, which is enabled by the microcontroller 760 via a control signal 814. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, and detecting cardiogenic impedance, etc. The impedance measuring circuit 812 is advantageously coupled to the switch 774 so that any desired electrode may be used, including the P4 electrode.

In the case where pacer/CRT 10 is intended to operate as an ICD device, it detects the occurrence of an arrhythmia, and automatically applies an appropriate electrical shock therapy to the heart aimed at terminating the detected arrhythmia. To this end, the microcontroller 760 further controls a shocking circuit 816 by way of a control signal 818. The shocking circuit 816 generates shocking pulses of low (up to 0.5 joules), moderate (0.5-10 joules) or high energy (11 to 40 joules or more), as controlled by the microcontroller 760. Such shocking pulses are applied to the heart of the patient through at least two shocking electrodes, and as shown in this embodiment, selected from the left atrial coil electrode 728, the RV coil electrode 736, and/or the SVC coil electrode 738. The housing 740 may act as an active electrode in combination with the RV electrode 736, or as part of a split electrical vector using the SVC coil electrode 738 or the left atrial coil electrode 728 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules or more), delivered asynchronously (since R-waves may be too disorganized), and pertaining exclusively to the treatment of fibrillation. Accordingly, the microcontroller 760 is capable of controlling synchronous or asynchronous delivery of shocking pulses.

An internal warning device 799 may be provided for generating perceptible warning signals to the patient via vibration, voltage or other methods.

Insofar as event discrimination is concerned, the microcontroller includes a P4 vector selection system 801 operative to select one or more P4 vectors for use in event discrimination, such as the P4 unipolar vector, P4-RV ring vector or the P4-D1 vector. An RA event discrimination controller 803 is provided to discriminate events sensed in the RA by examining signals on the selected P4 channel in accordance, e.g., with the techniques of FIGS. 5-7. To this end, the RA event discrimination controller includes a P4 event template comparison system 805 for comparing events sensed on P4 to known atrial and ventricular events, an RA event identification system 807 for identifying the RA event based on the template analysis, and an atrial tachycardia detection system 809 operative to confirm and respond to a possible AT. Additionally, a dynamic PVARP adjustment system 811 adjusts the PVARP, if appropriate, using the techniques already described.

An RV event discrimination controller 813 is provided to discriminate events sensed in the RV by examining signals on the selected P4 channel in accordance, e.g., with the techniques of FIGS. 8-9. To this end, the RV event discrimination controller includes a P4 event template comparison system 815 for comparing events sensed on P4 to known ventricular events such as R-waves and T-waves, an RV event identification system 817 for identifying the RV event based on the template analysis, and an ventricular tachycardia detection system 819 operative to confirm and respond to a possible VT/SVT. This may be performed in conjunction with a VT/SVT discriminator 829. Additionally, a dynamic VREF adjustment system 821 adjusts the VREF, if appropriate, using the techniques already described.

Template maintenance is performed by an on-board template generation and maintenance system 823 or an external template generation and maintenance system 825 within programmer 16 (or within other external devices). Therapy, diagnostics and warnings are controlled by system 827, which also controls delivery of CRT, where appropriate.

Hence, various components are incorporated into the pacer/CRT that provide: a primary sensing channel system operative to sense cardioelectrical events along a primary sensing channel connected to one or more of a RA lead and a RV lead, the events sensed using the primary sensing channel including near-field events and other events; a secondary sensing channel system operative to sense cardioelectrical events along a secondary sensing channel connected to the proximal electrode of the LV lead, the events sensed using the secondary sensing channel including both atrial events and ventricular events; and a proximal LV electrode-based discrimination system operative to discriminate near-field events from other events on the primary sensing channel based on the atrial and ventricular events sensed along the secondary sensing channel connected to the proximal electrode of the LV lead.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like. As noted, at least some of the techniques described herein can be performed by (or under the control of) an external device, such as programmer 16.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device equipped with a set of leads including a left ventricular (LV) lead having at least one proximal electrode implanted at a location sufficient to sense both atrial and ventricular events as substantially near-field events, the method comprising:
sensing cardioelectrical events along a primary sensing channel connected to one or more of a right atrial (RA) lead and a right ventricular (RV) lead, the events sensed using the primary sensing channel including near-field events and other events;
sensing cardioelectrical events along a secondary sensing channel connected to the proximal electrode of the LV lead, the events sensed using the secondary sensing channel including both atrial events and ventricular events;
discriminating near-field events from other events on the primary sensing channel based on the atrial and ventricular events sensed along the secondary sensing channel connected to the proximal electrode of the LV lead.

2. The method of claim 1 wherein the primary sensing channel is an RA channel connected to the RA lead and wherein the step of discriminating near-field events from other events on the primary RA sensing channel includes discriminating near-field atrial events on the RA channel from far-field ventricular events.

3. The method of claim 2 wherein discriminating near-field atrial events from far-field ventricular events on the RA channel includes discriminating among far-field ectopic ventricular events, far-field non-ectopic ventricular events and near-field atrial events.

4. The method of claim 2 wherein the events sensed on the primary RA channel and the events sensed on the secondary sensing channel are sensed substantially contemporaneously.

5. The method of claim 4 wherein discriminating near-field atrial events from far-field ventricular events on the RA channel includes comparing the events sensed contemporaneously on the secondary sensing channel with templates representative of known atrial and ventricular events to identify the origin of the events sensed on the RA channel.

6. The method of claim 5 wherein the events sensed on the secondary sensing channel are compared against atrial templates representative of events of atrial origin and against ventricular templates representative of events of ventricular origin.

7. The method of claim 6 wherein, if the events sensed on the secondary sensing channel do not substantially match either the atrial or ventricular templates, the contemporaneous events detected on the RA channel are identified as far-field ectopic ventricular events.

8. The method of claim 7 wherein, in response to detection of a far-field ectopic ventricular event, a premature ventricular contraction (PVC) counter is incremented.

9. The method of claim 6 wherein, if the events sensed on the secondary sensing channel substantially match the ventricular template, the contemporaneous events detected on the RA channel are identified as far-field non-ectopic ventricular events.

10. The method of claim 9 wherein, in response to detection of a far-field non-ectopic ventricular event near an atrial refractory period, the atrial refractory period is extended.

11. The method of claim 6 wherein, if the events sensed on the secondary sensing channel substantially match the atrial template, the contemporaneous events detected on the RA channel are identified as near-field atrial events.

12. The method of claim 11 wherein, in response to detection of a near-field atrial event near an atrial refractory period, the atrial refractory period is shortened.

13. The method of claim 11 wherein, in response to detection of a near-field atrial event near an atrial refractory period, an atrial tachycardia (AT) detection mode is activated.

14. The method of claim 2 wherein discriminating near-field atrial events on the RA channel from far-field ventricular events includes discriminating near-field atrial events representative of atrial tachyarrhythmias from far-field ventricular events.

15. The method of claim 14 wherein discriminating near-field atrial events representative of atrial tachyarrhythmias from far-field ventricular events is based on one or more of event timing and event morphology.

16. The method of claim 2 wherein the secondary sensing channel includes one or more of a proximal LV electrode unipolar sensing channel and a proximal LV electrode-RV electrode bipolar sensing vector.

17. The method of claim 1 wherein the primary sensing channel is an RV channel connected to the RV lead and wherein the step of discriminating near-field events from other events on the primary RV sensing channel includes discriminating near-field RV events on the RV channel from other ventricular events.

18. The method of claim 17 wherein discriminating near-field RV events on the RV channel from other ventricular events includes discriminating among normal near-field RV depolarization events (RV R-waves), far-field LV repolarization ventricular events (LV T-waves), far-field LV depolarization ventricular events (LV R-waves), abnormal ventricular events, and abnormal ventricular repolarization events.

19. The method of claim 17 wherein the events sensed on the primary RV channel and the events sensed on the secondary sensing channel are sensed substantially contemporaneously.

20. The method of claim 19 wherein discriminating near-field events from other events on the RV channel includes comparing the events sensed contemporaneously on the secondary sensing channel with templates representative of far-field and near-field ventricular events to identify the origin of the events sensed on the RV channel.

21. The method of claim 20 wherein the events sensed on the secondary sensing channel are compared against templates representative of normal near-field RV depolarization events (RV R-waves) and, if there is a substantial match, the events sensed on the secondary sensing channel are identified as near-field RV R-waves.

22. The method of claim 21 wherein, in response to detection of near-field RV R-waves near an RV refractory window, R-R intervals are measured to detect a possible ventricular tachyarrhythmia and discriminate between a tachycardia of ventricular origin and one of supraventricular origin.

23. The method of claim 21 wherein the events sensed on the secondary sensing channel are then compared against templates representative of far-field LV repolarization events (LV T-waves) and, if there is a substantial match, the events sensed on the secondary sensing channel are identified as far-field LV T-waves.

24. The method of claim 23 wherein, in response to detection of far-field LV R-waves near a ventricular refractory window (VREF), the ventricular refractory window is extended.

25. The method of claim 23 wherein the events sensed on the secondary sensing channel are then compared against templates representative of far-field LV depolarization ventricular events (LV R-waves) and, if there is a substantial match, the events sensed on the secondary sensing channel are identified as far-field LV R-waves.

26. The method of claim 25 wherein, in response to detection of far-field LV R-waves near a ventricular refractory window (VREF), the ventricular refractory window is extended.

27. The method of claim 26 wherein a slew rate of the events sensed on the secondary sensing channel is detected and compared against a threshold representative of an abnormal ventricular event and, if the slew rate exceeds the threshold, the events sensed on the secondary sensing channel are identified as abnormal ventricular depolarization events.

28. The method of claim 27 wherein, in response to detection of abnormal ventricular depolarization events near a ventricular refractory window (VREF), the ventricular refractory window is shortened and a ventricular tachyarrhythmia (VT) detection mode is activated.

29. The method of claim 27 wherein, if the slew rate does not exceed the threshold, the events sensed on the secondary sensing channel are identified as abnormal repolarization ventricular events.

30. The method of claim 29 wherein, in response to detection of abnormal ventricular repolarization events near a ventricular refractory window (VREF), the ventricular refractory window is extended and a ventricular repolarization diagnostics mode is activated.

31. The method of claim 17 wherein discriminating near-field events from other events on the primary RV sensing channel includes discriminating ventricular tachyarrhythmias from far-field ventricular oversensed events.

32. The method of claim 31 wherein discriminating ventricular tachyarrhythmias from far-field ventricular oversensing events is based on one or more of event timing, event morphology and event slew rate.

33. The method of claim 17 wherein the secondary sensing channel includes one or more of a proximal LV electrode unipolar sensing channel and a proximal LV electrode-distal LV electrode bipolar sensing vector.

34. The method of claim 1 wherein discriminating near-field events from other events on the primary sensing channel based on events sensed along the secondary sensing channel is performed using comparison templates and wherein the templates are adjustable using one or more of automatic updates and on-demand updates.

35. The method of claim 1 further including dynamically adjusting one or more of an atrial refractory period and a ventricular blanking period in response to discriminating the near-field events from far-field events on the primary sensing channel.

36. The method of claim 35 wherein dynamically adjusting one or more of an atrial refractory period and a ventricular blanking period is performed with hysteresis.

37. The method of claim 1 further including detecting a cardiac arrhythmia following discrimination of the near-field events from far-field events on the primary sensing channel.

38. The method of claim 37 further including controlling therapy in response to the cardiac arrhythmia.

39. A system for use with an implantable medical device equipped with a set of leads including a left ventricular (LV) lead having at least one proximal electrode implanted at a location sufficient to sense both atrial and ventricular events as substantially near-field events, the system comprising:
 a primary sensing channel system operative to sense cardioelectrical events along a primary sensing channel connected to one or more of a right atrial (RA) lead and a right ventricular (RV) lead, the events sensed using the primary sensing channel including near-field events and other events;
 a secondary sensing channel system operative to sense cardioelectrical events along a secondary sensing channel connected to the proximal electrode of the LV lead, the events sensed using the secondary sensing channel including both atrial events and ventricular events;
 a proximal LV electrode-based discrimination system operative to discriminate near-field events from other events on the primary sensing channel based on the atrial and ventricular events sensed along the secondary sensing channel connected to the proximal electrode of the LV lead.

40. A system for use with an implantable medical device equipped with a set of leads including a left ventricular (LV) lead having at least one proximal electrode implanted at a location sufficient to sense both atrial and ventricular events as substantially near-field events, the system comprising:
 means for sensing cardioelectrical events along a primary sensing channel connected to one or more of a right atrial (RA) lead and a right ventricular (RV) lead, the events sensed using the primary sensing channel including near-field events and other events;
 means for sensing cardioelectrical events along a secondary sensing channel connected to the proximal electrode of the LV lead, the events sensed using the secondary sensing channel including both atrial events and ventricular events;
 means for discriminating near-field events from other events on the primary sensing channel based on the atrial and ventricular events sensed along the secondary sensing channel connected to the proximal electrode of the LV lead.

* * * * *